US012788470B2

(12) United States Patent
Lafay et al.

(10) Patent No.: US 12,788,470 B2
(45) Date of Patent: Nov. 10, 2026

(54) TESTING ELECTROSURGICAL GENERATORS

(71) Applicant: Cilag GmbH International, Zug (CH)

(72) Inventors: Eric Lafay, Cincinnati, OH (US); Zachary Leavitt, Asheville, NC (US)

(73) Assignee: CILAG GMBH INTERNATIONAL, Zug (CH)

( * ) Notice: Subject to any disclaimer, the term of this patent is extended or adjusted under 35 U.S.C. 154(b) by 278 days.

(21) Appl. No.: 18/495,222

(22) Filed: Oct. 26, 2023

(65) Prior Publication Data

US 2025/0134576 A1 May 1, 2025

(51) Int. Cl.
*A61B 18/12* (2006.01)
*G01R 31/28* (2006.01)
*A61B 18/00* (2006.01)

(52) U.S. Cl.
CPC ...... *A61B 18/1206* (2013.01); *A61B 18/1233* (2013.01); *G01R 31/282* (2013.01); *A61B 2018/00755* (2013.01); *A61B 2018/00988* (2013.01); *A61B 2560/0223* (2013.01)

(58) Field of Classification Search
CPC ........... A61B 2018/00755; A61B 2018/00875; A61B 2018/00988; A61B 18/1206; A61B 18/1233
See application file for complete search history.

(56) References Cited

U.S. PATENT DOCUMENTS 5,540,722 A * 7/1996 Clare ..................... A61B 18/14 600/522
7,112,201 B2 9/2006 Truckai et al.
7,169,145 B2 1/2007 Isaacson et al.
8,771,270 B2 7/2014 Burbank
8,986,302 B2 3/2015 Aldridge et al.
9,055,961 B2 6/2015 Manzo et al.
9,119,657 B2 9/2015 Shelton, IV et al.
9,192,425 B2 * 11/2015 Behnke, II ......... A61B 18/1206
10,010,366 B2 7/2018 Strobl
10,335,129 B2 7/2019 Boudreaux
10,667,856 B2 6/2020 Felder et al.
(Continued)

OTHER PUBLICATIONS

Keysight, "Why is the segmented memory acquisition mode useful and which Infiniium oscilloscopes support it?" dated no later than Oct. 23, 2023, available at <https://edadocs.software.keysight.com/kkbopen/why-is-the-segmented-memory-acquisition-mode-useful-and-which-infiniium-oscilloscopes-support-it-589746227.html>.
(Continued)

*Primary Examiner* — Michael F Peffley
*Assistant Examiner* — Samantha M Good
(74) *Attorney, Agent, or Firm* — FBT Gibbons LLP

(57) ABSTRACT

Various exemplary systems, devices, and methods for testing electrosurgical generators are provided. In general, an electrosurgical generator is configured to generate energy and provide the energy to an electrosurgical instrument. In an exemplary embodiment, testing of an electrosurgical generator includes simulating a tissue load being electrosurgically treated in a surgical procedure. The simulated tissue load is simulated by a computer system that includes a circuit that has a plurality of states each corresponding to a different simulated tissue load. The circuit is configured to change between the plurality of states during the testing so as to simulate a plurality of different tissue loads.

19 Claims, 14 Drawing Sheets

(56) References Cited

U.S. PATENT DOCUMENTS

| | | | |
|---|---|---|---|
| 10,932,808 | B2 | 3/2021 | Shelton, IV et al. |
| 11,241,269 | B2 | 2/2022 | Brady et al. |
| 11,266,430 | B2 | 3/2022 | Clauda et al. |
| 11,317,937 | B2 | 5/2022 | Nott et al. |
| 11,529,187 | B2 | 12/2022 | Shelton, IV et al. |
| 11,602,393 | B2 | 3/2023 | Shelton, IV et al. |
| 2019/0274748 | A1 | 9/2019 | Danzinger et al. |
| 2022/0313341 | A1 | 10/2022 | Wiener et al. |

OTHER PUBLICATIONS

Rohde & Schwartz, "History & segmented memory software," dated no later than Oct. 23, 2023, available at <https://www.rohde-schwarz.com/us/products/test-and-measurement/general-analysis/history-segmented-memory-software_63493-504580.html>.

Tektronix, "Using FastFrame™ Segmented Memory," 2010, available at <https://download.tek.com/document/55W_12112_2.pdf>.

Teledyne LeCroy, "Sequence Mode in HDO Oscilloscopes," Oct. 19, 2012, available at <https://www.teledynelecroy.com/doc/sequence-mode-in-hdo-oscilloscopes>.

Yokogawa Test & Measurement Corporation, "DLM2000 Series—History Memory," dated no later than Oct. 23, 2023, available at <https://tmi.yokogawa.com/library/videos/product-overviews/dlm2000-series-history-memory/>.

* cited by examiner

TESTING ELECTROSURGICAL GENERATORS

FIELD

The present disclosure relates generally to testing electrosurgical generators.

BACKGROUND

Electrosurgical instruments use energy to affect tissue. Electrosurgical instruments include devices with tissue-contacting electrodes, such as an electrosurgical instrument having one or more electrodes. Monopolar electrosurgical instruments have one electrode. Bipolar surgical instruments have two electrodes (active and return electrodes). In use, energy is supplied to the electrosurgical instrument by an electrosurgical generator that generates oscillating electric currents to energize the electrosurgical instrument's electrode(s).

The energy supplied to an electrosurgical instrument from an electrosurgical generator may be in the form of radio frequency ("RF") energy. RF energy is a form of electrical energy that may be in a frequency range of 300 kHz to 1 MHz for surgical applications. In use, an electrosurgical instrument can transmit low frequency RF energy through tissue, which causes ionic agitation, or friction, in effect resistive heating, thereby increasing the temperature of the tissue. Because a sharp boundary may be created between the affected tissue and the surrounding tissue, surgeons can operate with a high level of precision and control, without sacrificing non-targeted adjacent tissue. The low operating temperatures of RF energy may be useful for removing, shrinking, or sculpting soft tissue while simultaneously sealing the tissue, e.g., blood vessels. RF energy may work particularly well on connective tissue, which is primarily comprised of collagen and shrinks when contacted by heat.

Because heat is applied to tissue being sealed, various characteristics of the tissue, such as impedance, change as the tissue increases in temperature, water evaporates, etc. Electrosurgical generators may be able to monitor tissue impedance during energy delivery and adjust the energy accordingly per preprogrammed algorithms to maintain effective tissue sealing.

To help ensure that electrosurgical generators adjust energy appropriately, electrosurgical generators may be tested prior to use, typically in a laboratory or manufacturing setting prior to sale to end users. It is not feasible to perform all desired testing of all desired electrosurgical generators with an actual tissue load during performance of an actual surgical procedure. However, it is difficult to simulate a tissue load for electrosurgical generator testing because of the number of variables that affect tissue during energy application, such as a type of the tissue, a thickness of the tissue, amount of water or saline present, etc. Electrosurgical generator testing can therefore result in inaccurate or incomplete simulated tissue load scenarios such that the preprogrammed algorithms of tested electrosurgical generators do not maintain tissue sealing as effectively as desired.

Accordingly, there remains a need for improved testing of electrosurgical generators.

SUMMARY

In general, systems, devices, and methods for testing electrosurgical generators are provided.

In one aspect, an electrosurgical generator testing system is provided that in one embodiment includes a simulated tissue load configured to be operatively coupled to an electrosurgical generator configured to deliver energy to an electrosurgical instrument. The simulated tissue load includes a circuit, a processor, and a memory. The circuit includes a first plurality of relays and a plurality of resistive components. The plurality of resistive components are arranged in parallel, and each of the plurality of relays is operatively coupled to an associated one of the plurality of resistive components such that each of the plurality of resistive components is either enabled or disabled based on a state of its associated one of the first plurality of relays. The memory stores instructions that, when executed by the processor, cause the processor to perform operations including, with the simulated tissue load receiving an energy signal from the electrosurgical generator, controlling the state of each of the first plurality of relays so as to sequentially simulate each of a plurality of target tissue loads defined by a plurality of predefined parameters stored in the memory, and generating a report indicative of settings of the electrosurgical generator for each of the simulated plurality of target tissue loads.

The electrosurgical generator testing system can have any number of variations. For example, the simulated tissue load can also include an additional resistive component having a fixed resistance, and the additional resistive component can be arranged in parallel with the plurality of resistive components. Further, each of the additional resistive component and the plurality of resistive components can include a resistor.

For another example, the simulated tissue load can also include a second plurality of relays and a plurality of capacitive components, and the plurality of capacitive components can be arranged in parallel with each other and with the plurality of resistive components. Further, the simulated tissue load can also include an additional capacitive component having a fixed capacitance, and the additional capacitive component can be arranged in parallel with the plurality of capacitive components. Further, each of the additional capacitive component and the plurality of capacitive components can include a capacitor.

For yet another example, the plurality of resistive components can include a number of resistive components in a range of four to thirty-two, and each of the plurality of resistive components can include a resistor.

For still another example, the setting of the electrosurgical generator for each of the simulated plurality of target tissue loads can be either: automatically selected through the controlling of the state of each of the first plurality of relays, or manually selected by a user. Further, the operations can also include prompting the user to manually select the setting of the electrosurgical generator for one of the simulated plurality of target tissue loads in response to the setting of the electrosurgical generator for the one of the simulated plurality of target tissue loads being unable to be automatically selected through the controlling of the state of each of the first plurality of relays.

For another example, the electrosurgical generator testing system can also include the electrosurgical generator.

For still another example, the electrosurgical generator testing system can also include a data acquisition system (DAQ) configured to be operatively coupled to the simulated tissue load and to display information indicative of data in the generated report. Further, the electrosurgical generator testing system can also include the electrosurgical generator.

In another aspect, a method of testing electrosurgical generators is provided that in one embodiment includes receiving an electrical signal from an electrosurgical generator at a circuit of a simulated tissue load. The circuit includes a first plurality of relays and a plurality of resistive components. The plurality of resistive components are arranged in parallel. Each of the plurality of relays is operatively coupled to an associated one of the plurality of resistive components such that each of the plurality of resistive components is either enabled or disabled based on a state of its associated one of the first plurality of relays. The method also includes, with the simulated tissue load receiving the energy signal from the electrosurgical generator, controlling, using a processor, the state of each of the first plurality of relays so as to sequentially simulate each of a plurality of target tissue loads defined by a plurality of predefined parameters stored in a memory of the simulated tissue load. The method also includes generating, using the processor, a report indicative of settings of the electrosurgical generator for each of the simulated plurality of target tissue loads.

The method can vary in any number of ways. For example, the simulated tissue load can also include an additional resistive component having a fixed resistance, and the additional resistive component can be arranged in parallel with the plurality of resistive components. Further, each of the additional resistive component and the plurality of resistive components can include a resistor.

For another example, the simulated tissue load can also include a second plurality of relays and a plurality of capacitive components, and the plurality of capacitive components can be arranged in parallel with each other and with the plurality of resistive components. Further, the simulated tissue load can also include an additional capacitive component having a fixed capacitance, and the additional capacitive component can be arranged in parallel with the plurality of capacitive components. Further, each of the additional capacitive component and the plurality of capacitive components can include a capacitor.

For yet another example, the plurality of resistive components can include a number of resistive components in a range of four to thirty-two, and each of the plurality of resistive components can include a resistor.

For still another example, the setting of the electrosurgical generator for each of the simulated plurality of target tissue loads can be either automatically selected through the controlling of the state of each of the first plurality of relays, or manually selected by a user. Further, the method can also include prompting, using the processor, the user to manually select the setting of the electrosurgical generator for one of the simulated plurality of target tissue loads in response to the setting of the electrosurgical generator for the one of the simulated plurality of target tissue loads being unable to be automatically selected through the controlling of the state of each of the first plurality of relays.

For another example, the method can also include displaying, on a data acquisition system (DAQ) operatively coupled to the simulated tissue load, information indicative of data in the generated report.

In another aspect, a non-transitory computer program product storing instructions which, when executed by a processor, cause the processor to implement operations including, with a simulated tissue load receiving an energy signal from the electrosurgical generator, controlling a state of each of a first plurality of relays of the simulated tissue load so as to sequentially simulate each of a plurality of target tissue loads defined by a plurality of predefined parameters stored in a memory of the simulated tissue load. The circuit includes the first plurality of relays and a plurality of resistive components. The plurality of resistive components are arranged in parallel. Each of the plurality of relays is operatively coupled to an associated one of the plurality of resistive components such that each of the plurality of resistive components is either enabled or disabled based on a state of its associated one of the first plurality of relays. The operations also include generating a report indicative of settings of the electrosurgical generator for each of the simulated plurality of target tissue loads.

The non-transitory computer program product can vary in any number of ways. For example, the simulated tissue load can also include an additional resistive component having a fixed resistance, and the additional resistive component can be arranged in parallel with the plurality of resistive components. Further, each of the additional resistive component and the plurality of resistive components can include a resistor.

For another example, the simulated tissue load can also include a second plurality of relays and a plurality of capacitive components, and the plurality of capacitive components can be arranged in parallel with each other and with the plurality of resistive components. Further, the simulated tissue load can also include an additional capacitive component having a fixed capacitance, and the additional capacitive component can be arranged in parallel with the plurality of capacitive components. Further, each of the additional capacitive component and the plurality of capacitive components can include a capacitor.

For yet another example, the plurality of resistive components can include a number of resistive components in a range of four to thirty-two, and each of the plurality of resistive components can include a resistor.

For still another example, the setting of the electrosurgical generator for each of the simulated plurality of target tissue loads can be either automatically selected through the controlling of the state of each of the first plurality of relays, or manually selected by a user. Further, the operations can also include prompting, using the processor, the user to manually select the setting of the electrosurgical generator for one of the simulated plurality of target tissue loads in response to the setting of the electrosurgical generator for the one of the simulated plurality of target tissue loads being unable to be automatically selected through the controlling of the state of each of the first plurality of relays.

For another example, the operations can also include displaying, on a data acquisition system (DAQ) operatively coupled to the simulated tissue load, information indicative of data in the generated report.

BRIEF DESCRIPTION OF DRAWINGS

The present invention is described by way of reference to the accompanying figures which are as follows.

DETAILED DESCRIPTION

Figure 1:
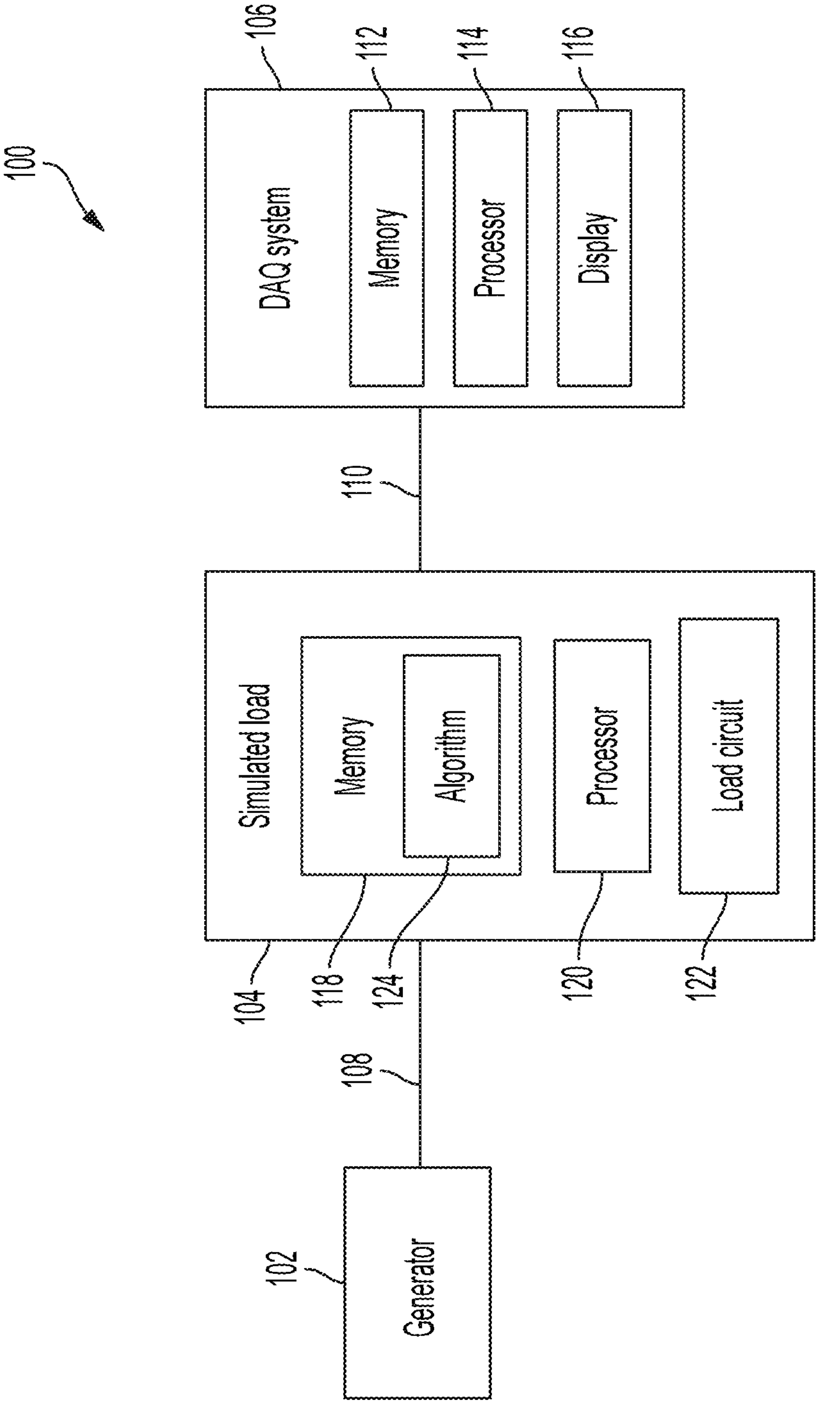
FIG. 1 is a schematic view of one embodiment of a testing system for an electrosurgical generator.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Various exemplary systems, devices, and methods for testing electrosurgical generators are provided. In general, an electrosurgical generator is configured to generate energy and provide the energy to an electrosurgical instrument (also referred to herein as an "electrosurgical tool"). The electrosurgical instrument is configured to use energy received from the electrosurgical generator in treating tissue engaged by the electrosurgical instrument during performance of a surgical procedure on a patient, such as by delivering the energy to the tissue via at least one electrode of the electrosurgical instrument to seal and/or cut the tissue.

In an exemplary embodiment, testing of an electrosurgical generator includes simulating a tissue load being electrosurgically treated in a surgical procedure. The simulated tissue load is simulated by a computer system that includes a circuit that has a plurality of states each corresponding to a different simulated tissue load. The circuit is configured to change between the plurality of states during the testing so as to simulate a plurality of different tissue loads. The computer system including the tissue load is configured to be in operative communication with the electrosurgical generator during the testing. Energy received by the computer system can thus be tested with the circuit in different states so as to simulate performance for a variety of different possible tissue loads. The computer system (or other computer system in operative communication therewith) is configured to log and/or display the performance results to allow for the electrosurgical generator to be programmed to compensate for various changes in tissue conditions that may occur during treatment of the tissue, e.g., due to the application of heat to the tissue. The electrosurgical generator may therefore be preprogrammed to maintain effective tissue treatment, such as tissue sealing and/or cutting, by an electrosurgical instrument during real world use of the electrosurgical generator that occurs after the testing. Testing typically occurs in a laboratory or manufacturing setting prior to sale of an electrosurgical generator to a hospital or an end user.

In some embodiments, the electrosurgical generator is configured to generate only electrosurgical energy, such as radio frequency (RF) energy. In other embodiments, the electrosurgical generator is a multi-functional generator configured to generate electrosurgical energy and another type of energy, such as ultrasonic energy.

Various embodiments of electrosurgical tools and/or electrosurgical generators are described further in, for example, U.S. Pat. No. 7,112,201 entitled "Electrosurgical Instrument And Method Of Use" issued on Sep. 26, 2006, U.S. Pat. No. 7,169,145 entitled "Tuned Return Electrode With Matching Inductor" issued on Jan. 30, 2007, U.S. Pat. No. 8,771,270 entitled "Bipolar Cautery Instrument" issued on Jul. 8, 2014, U.S. Pat. No. 8,986,302 entitled "Surgical Generator For Ultrasonic And Electrosurgical Devices" issued on Mar. 24, 2015, U.S. Pat. No. 9,055,961 entitled "Fusing And Cutting Surgical Instrument And Related Methods" issued on Jun. 16, 2015, U.S. Pat. No. 9,119,657 entitled "Rotary Actuatable Closure Arrangement For Surgical End Effector" issued on Sep. 1, 2015, U.S. Pat. No. 10,010,366 entitled "Surgical Devices And Methods For Tissue Cutting And Sealing" issued on Jul. 3, 2018, U.S. Pat. No. 10,335,129 entitled "Methods And Devices For Auto Return Of Articulated End Effectors" issued on Jul. 2, 2019, U.S. Pat. No. 10,667,856 entitled "Robotic Bi-Polar Instruments" issued on Jun. 2, 2020, U.S. Pat. No. 10,932,808 entitled "Methods, Systems, And Devices For Controlling Electrosurgical Tools" issued on Mar. 2, 2021, U.S. Pat. No. 11,241,269 entitled "Surgical Devices Switchable Between Monopolar Functionality And Bipolar Functionality" issued on Feb. 8, 2022, U.S. Pat. No. 11,266,430 entitled "End Effector Control And Calibration" issued on Mar. 8, 2022, U.S. Pat. No. 11,317,937 entitled "Determining The State Of An Ultrasonic End Effector" issued on May 3, 2022, U.S. Pat. No. 11,529,187 entitled "Surgical Evacuation Sensor Arrangements" issued on Dec. 20, 2022, U.S. Pat. No. 11,602,393 entitled "Surgical Evacuation Sensing And Generator Control" issued on Mar. 14, 2023, U.S. Patent Application Publication No. 2019/0274748 entitled "Measuring Impedance For Electrosurgical Tools" published on Sep. 12, 2019, and U.S. Patent Application Publication No. 2022/0313341 entitled "Surgical Proceduralization Via Modular Energy System" published on Oct. 6, 2022, which are hereby incorporated by reference in their entireties.

FIG. 1 illustrates one embodiment of a testing system 100 for testing electrosurgical generators. The testing system 100 is configured to simulate a tissue load being electrosurgically treated in a surgical procedure. Different simulated tissue loads can correspond to different combinations of tissue characteristics such as tissue type (e.g., stomach tissue, uterine tissue, carotid artery, etc.), tissue thickness, tissue impedance, etc.

The testing system 100 includes an electrosurgical generator (also referred to herein as a "generator") 102, a simulated load (also referred to herein as a "simulated tissue load") 104, and a data acquisition system (DAQ) system 106. The generator 102 is configured to be in operative communication with the simulated load 104 via a first communication link 108. The simulated load 104 is configured to be in operative communication with the DAQ system 106 via a second communication link 110. The first and second communication links 108, 110 each can be a wired connection (using a cable, etc.) or can be a wireless connection (e.g., using Wi-Fi, Bluetooth, etc.). Both of the first and second communication links 108, 110 can be wired, both of the first and second communication links 108, 110 can be wireless, or one of the first and second communication links 108, 110 can be wired and the other of the first and second communication links 108, 110 can be wireless.

The DAQ system 106 is configured to receive data and display information during testing of the generator 102. As in this illustrated embodiment, the DAQ system 106 can be implemented as a computer system that includes a memory 112, a processor 114 configured to execute instructions stored in the memory 112, and a display 116 configured to show information thereon. The DAQ system 106 can be an oscilloscope, an analyzer, or other type of electronic test equipment.

The generator 102 is configured to generate energy and provide the energy to an electrosurgical instrument, such as during performance of a surgical procedure on the patient. In the testing system 100, the generator 102 is configured to generate energy and provide the energy to the simulated load 104.

As in this illustrated embodiment, the simulated load 104 can be implemented as a computer system that includes a memory 118, a processor 120 configured to execute instructions stored in the memory 118, and a load circuit (also referred to herein as a "circuit") 122. The instructions stored in the memory 118 include an algorithm (also referred to herein as a "control algorithm") 124 configured to be executed by the processor 120 to control the load circuit 122 during generator testing. In an exemplary embodiment, the load circuit 122 includes binary resistive loads, electromechanical relays (also referred to herein as "relays"), and a series of parallel configuration resistive components configured to toggled by the electromechanical relays. Different combinations of on/off states of the electromechanical relays represent different loads that each simulate a different tissue load. The algorithm 124 defines which of the electromechanical relays to turn on/off over a time of testing such that the processor 120 is configured to cause states of various ones of the electromechanical relays to change over time in the course of a testing process to simulate a plurality of different tissue loads.

The simulated load 104 (e.g., the processor 120 thereof) is configured to output data from the load circuit 122 to the DAQ system 106, which can show data results on the display 114 and/or analyze data using the DAQ system's processor 110. The output data, such as that shown on the display 114, is configured to allow for determining which generator settings (e.g., voltage, current, impedance, etc.) achieve an expected output for a particular simulated tissue load.

In some embodiments, the DAQ system 106 is omitted and the simulated load 104 is configured to perform functions of the DAQ system 106 during testing of the electrosurgical generator 102.

Figure 2:
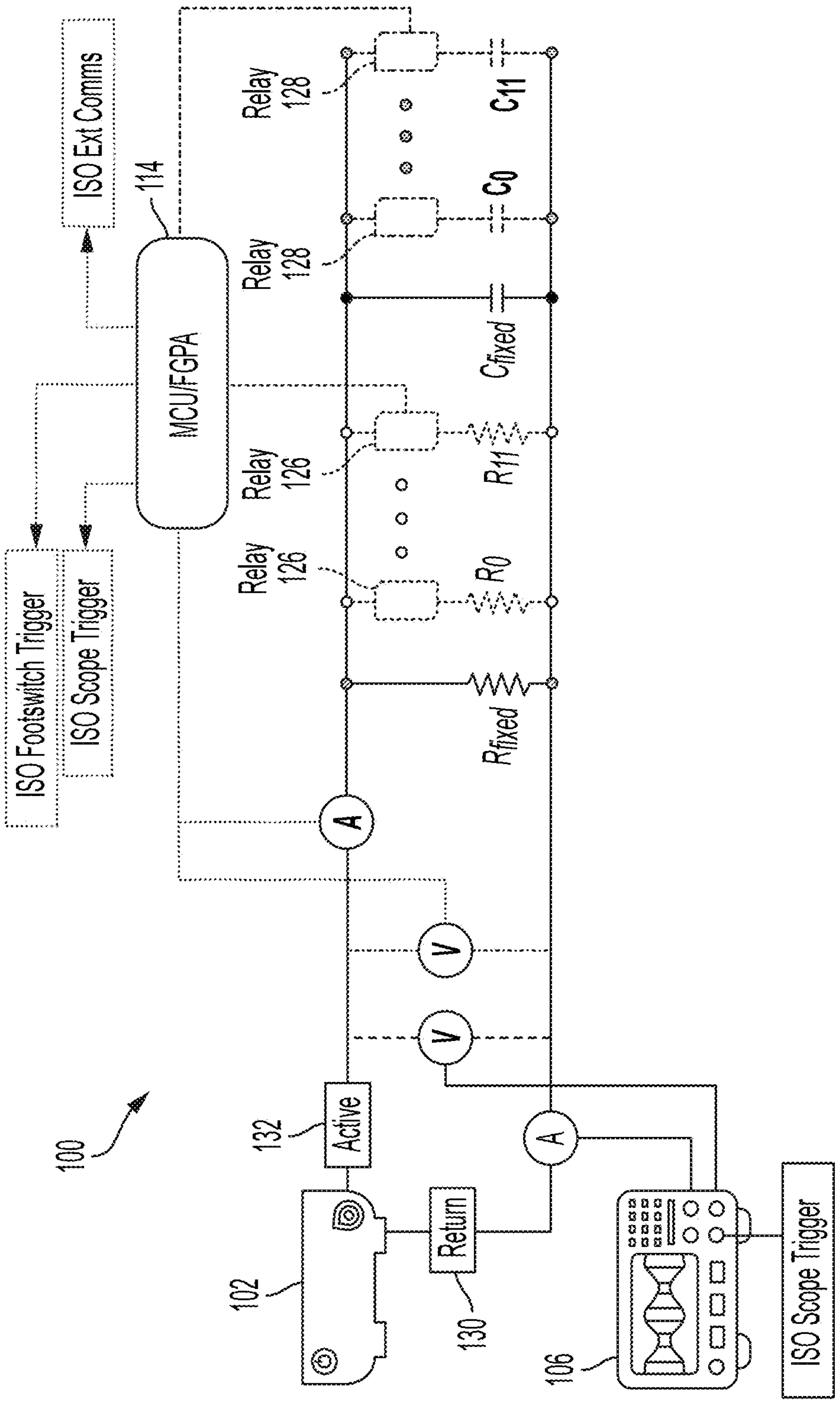
FIG. 2 is a schematic view of one embodiment of the testing system of FIG. 1.

FIG. 2 illustrates one embodiment of the testing system 100 including the generator 102, the simulated load 104, and the DAQ system 106. The DAQ system 106 in this illustrated embodiment is shown as an oscilloscope, but other DAQ systems can be used, such as analyzers or other type of electronic test equipment. The processor 120 of the simulated load 104 is shown in FIG. 2 as being either a microcontroller unit (MCU) or a field-programmable gate array (FPGA or FGPA), but as discussed herein, various other configurations of the processor 120 are possible.

In this illustrated embodiment, the simulated load 104 includes a fixed resistance, a binary resistance, a fixed capacitance, and a binary capacitance. The fixed resistance is a resistance configured to remain fixed during testing of the generator 102. The fixed resistance includes a resistive component $R_{fixed}$ having a fixed value. The fixed resistive component $R_{fixed}$ is a resistor in this illustrated embodiment. The fixed resistive component $R_{fixed}$ can be a thick film resistor, such as a TKH45 series resistor available from Ohmite Mfg. Co. of Warrenville, IL.

The binary resistance is a resistance configured to change during testing of the generator 102. The binary resistance includes a plurality of resistive components $R_0$ to $R_{11}$ each associated with one of a first plurality of relays 126. The plurality of resistive components $R_0$ to $R_{11}$ are a series of parallel configuration resistive components $R_0$ to $R_{11}$ configured to toggled by the first plurality of relays 126. The processor 120 is configured to control the on/off states of the first plurality of relays 126 according to the control algorithm 124, e.g., with binary value 1 indicating "on" and binary value 0 indicating "off." Each of the resistive components $R_0$ to $R_{11}$ in this illustrated embodiment is a resistor. The resistive components $R_0$ to $R_{11}$ can each be a thick film resistor, such as a TKH45 series resistor available from Ohmite Mfg. Co. of Warrenville, IL. The first plurality of relays 126 can each be a miniature relay, such as an APAN3013 general purpose relay or other general purpose relay available from Panasonic Electric Works Company of Tokyo, Japan.

The binary resistance includes twelve resistive components $R_0$ to Ru in this illustrated embodiment, but another number of resistive components for the binary resistance is possible. In an exemplary embodiment, the number of resistive components in the binary resistance is in a range between four and thirty-two such that the testing system is in a range of a 4-bit to a 32-bit testing system.

The testing system 100 of FIG. 2 is a 12-bit testing system because the simulated load 104 includes twelve resistive components $R_0$ to $R_{11}$ that each have a binary state defined by whether its associated one of the first plurality of relays 126 is on (relay switch closed and binary value 1) or off (relay switch open and binary value 0). The binary resistance including twelve resistive components $R_0$ to $R_{11}$ allows for enough space between adjacent resistance states of the binary resistance to allow for control between simulated tissue states. The binary resistance including less than twelve binary resistive components would allow for less control but would lower overall cost of the testing system 100 and/or reduce a length of the generator testing process. Actual tissue having energy applied thereto by an electro-surgical tool gradually moves between states as the tissue is heated. Having less space between adjacent resistance states of the binary resistance may allow for better simulation of actual tissue states because the binary resistance can be controlled by the processor 120 to move between adjacent states with relatively low resistance jump between the states while also providing better load sharing, less output ripple, and faster transitions than a generator testing system with less than twelve binary resistive components.

Figure 3:
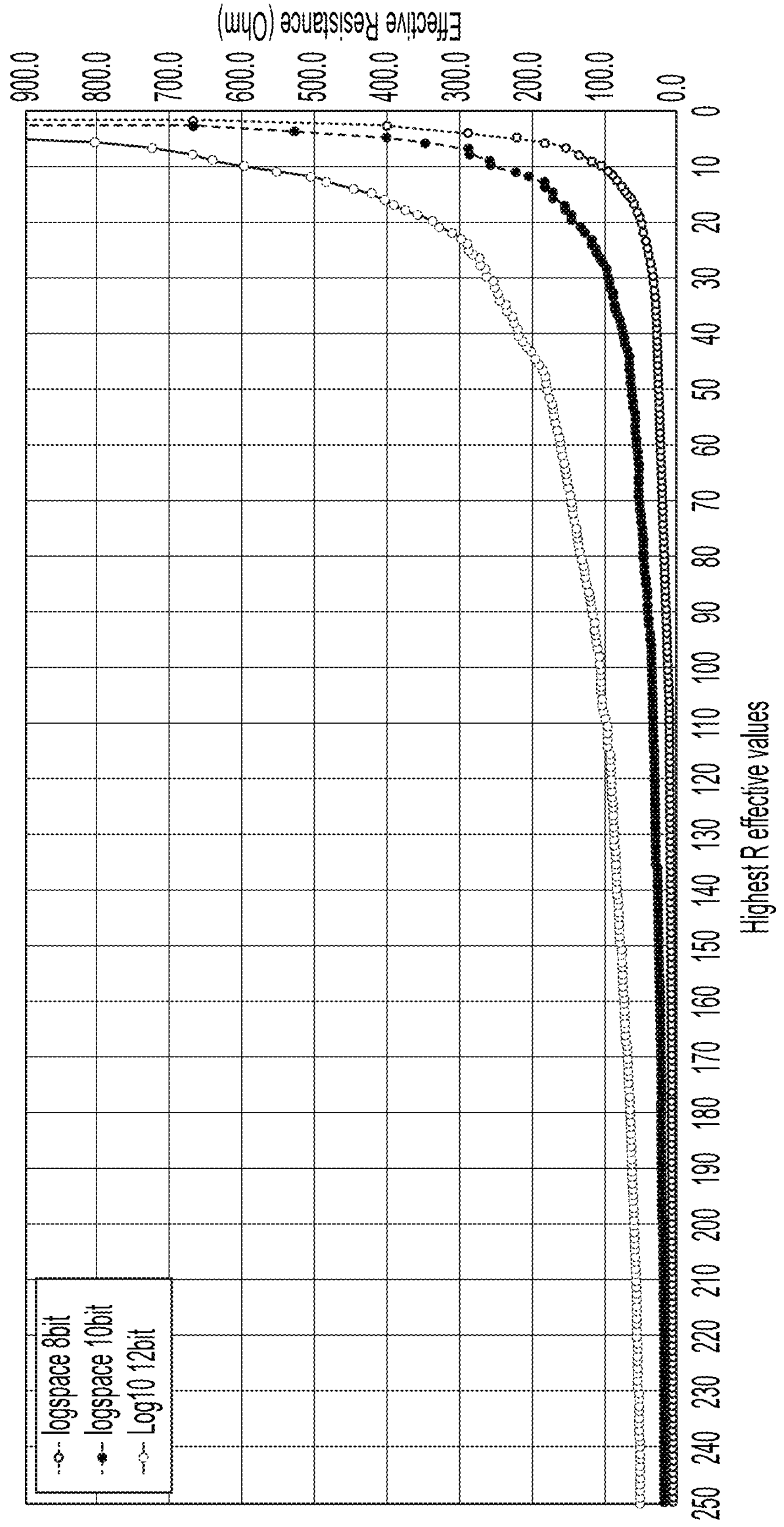
FIG. 3 is a graph showing one embodiment of highest effective resistance values versus effective resistance for 8-bit, 10-bit, and 12-bit binary resistive systems.

FIG. 3 illustrates one embodiment of a graph showing adjacent resistance states of the binary resistance of a 12-bit testing system (such as the 12-bit testing system of FIG. 2), adjacent resistance states of the binary resistance of a 10-bit testing system, and adjacent resistance states of the binary resistance of an 8-bit testing system. As effective resistance (Y axis) increases (e.g., as controlled by the processor 120 executing the algorithm 124 of FIG. 1), jumps (distances) between adjacent points on the 12-bit plot line (top plot line) are smaller than jumps between adjacent points on the 10-bit plot line (middle plot line), which has smaller jumps between adjacent points than on the 8-bit plot line (bottom plot line). The graph thus illustrates the greater control for a 12-bit testing system than for generator testing systems including a binary resistance with a fewer number of resistive components.

Adjacent points on a plot line in FIG. 3 represent different states of the binary resistance, with adjacent plot points being reached by changing one of the binary resistance's resistive components. Using the 12-bit testing system as an example, moving from the plot point at about 800 Ohms effective resistance (e.g., all of the first plurality of relays 126 of FIG. 2 off so only the fixed resistance is providing resistance) to the next lower plot point at about 725 Ohms can be achieved by changing the state of one of the first plurality of relays (e.g., all of the first plurality of relays 126 of FIG. 2 off except for the one of the first plurality of relays 126 associated with the lowest value resistor ($R_1$ in the example of Table 1 below) so only the fixed resistance and one binary resistive component are providing resistance).

The fixed resistance $R_{fixed}$ and the binary resistance's resistive components $R_0$ to $R_{11}$ can each have a variety of values. Table 1 shows one embodiment of resistance values (in Ohms) for the fixed resistance $R_{fixed}$ and the binary resistance's resistive components $R_0$ to $R_{11}$. In an exemplary embodiment, as in Table 1, each of the binary resistance's resistive components $R_0$ to $R_{11}$ has a different resistance value, which allows each combination of first plurality of relay 126 on/off states to have a different overall resistance value. If all of the first plurality of relays 126 are in an off state, the simulated load 104 will still have a resistance defined by the fixed resistive component $R_{fixed}$ and thus avoid a short circuit condition. In some embodiments, a fixed resistive component is omitted from a load circuit, but in such embodiments, a short circuit condition may result if all of the load circuit's binary resistance's resistive components are disabled, e.g., each of the resistive components' associated relays are off.

TABLE 1

| | $R_0$ | $R_1$ | $R_2$ | $R_3$ | $R_4$ | $R_5$ | $R_6$ | $R_7$ | $R_8$ | $R_9$ | $R_{10}$ | $R_{11}$ | $R_{fixed}$ |
|---|---|---|---|---|---|---|---|---|---|---|---|---|---|
| Resistance | 10 | 20 | 33.3 | 55.6 | 100 | 200 | 333.3 | 500 | 1000 | 1750 | 3200 | 5600 | 2000 |

Referring again to FIG. 2, the fixed capacitance is a capacitance configured to remain fixed during testing of the generator 102. The fixed capacitance includes a capacitive component $C_{fixed}$ having a fixed value. The fixed capacitive component $C_{fixed}$ is a capacitor in this illustrated embodiment.

The binary capacitance is a capacitance value configured to change during testing of the generator 102. The binary capacitance includes a plurality of capacitive components $C_0$ to $C_{11}$ each having an associated one of a second plurality of relays 128. Each of the capacitive components $C_0$ to $C_{11}$ in this illustrated embodiment is a capacitor. The plurality of capacitive components $C_0$ to $C_{11}$ are a series of parallel configuration capacitive components $C_0$ to $C_{11}$ configured to toggled by the second plurality of relays 128. The processor 120 is configured to control the on/off states of the second plurality of relays 128 according to the control algorithm 124, e.g., with binary value 1 indicating "on" and binary value 0 indicating "off." The second plurality of relays 128 can each be a miniature relay, such as an APAN3013 general purpose relay or other general purpose relay available from Panasonic Electric Works Company of Tokyo, Japan.

Table 2 shows one embodiment of capacitance values (in pF) for the fixed capacitance $C_{fixed}$ and the binary capacitance's capacitive components $C_0$ to $C_{11}$ that can be used, for example, with the resistance values of Table 1. In an exemplary embodiment, as in Table 2, each of the binary capacitance's capacitive components $C_0$ to $C_{11}$ has a different capacitance value, which allows each combination of second plurality of relay 128 on/off states to have a different overall capacitance value. If all of the second plurality of relays 128 are in an off state, the simulated load 104 will still have a capacitance defined by the fixed capacitive component $C_{fixed}$. The fixed capacitive component $C_{fixed}$ can thus be "tuned" or "trimmed" to remove any positive or negative induced phase shift caused by introduction of cabling or connection hardware. In an exemplary embodiment, a testing system's fixed capacitance (e.g., $C_{fixed}$ of FIG. 2) and capacitive components (e.g., capacitors $C_0$ to $C_{11}$ of FIG. 2) each have a value in a range of 20 pF to 5728 pF. In some embodiments, a fixed capacitive component is omitted from a load circuit, but in such embodiments, positive or negative induced phase shift may be present.

TABLE 2

| | $C_0$ | $C_1$ | $C_2$ | $C_3$ | $C_4$ | $C_5$ | $C_6$ | $C_7$ | $C_8$ | $C_9$ | $C_{10}$ | $C_{11}$ | $C_{fixed}$ |
|---|---|---|---|---|---|---|---|---|---|---|---|---|---|
| Capacitance | 22 | 33 | 56 | 82 | 120 | 180 | 240 | 390 | 560 | 820 | 1200 | 2000 | 25 |

The testing system 100 of FIG. 2 also illustrates locations of return and active electrodes 130, 132 of a bipolar electrosurgical instrument relative to the simulated load 104 and the generator 102. As will be appreciated by a person skilled in the art, energy (e.g., an electrical current) flows from the generator 102 and through the active electrode 132 to the load 104 and then flows through the return electrode 130 before returning to the generator 102 and to the DAQ system 106. The return and active electrodes 130, 132 can be included in the testing system 100 as part of an electrosurgical instrument or can be independent elements used in the testing system 100 for testing purposes.

FIG. 2 also shows that the DAQ system 106 includes a trigger (labeled "ISO Scope Trigger" in FIG. 2). The trigger is part of the oscilloscope and functions according to a oscilloscope's trigger system, as will be appreciated by those skilled in the art, such as by being manually actuated (e.g., button pressed, switch flipped, etc.) by a user. Actuation of the trigger is configured to trigger the DAQ system 106 to begin sampling the circuit signal and display information on the display 116 when the first and second plurality of relays 126, 128 have stabilized and are sensing power.

In an exemplary embodiment, a testing system's fixed resistance (e.g., $R_{fixed}$ of FIG. 2) and binary resistance's resistive components (e.g., resistive components $R_0$ to $R_{11}$ of FIG. 2) each have a resistance value in a range of 4.5 Ohms to 2000 Ohms since the generator's terminals and/or the electrosurgical instruments electrodes 130, 132 typically experience a resistance in a range of 4.5 Ohms to 2000 Ohms.

Figure 4:
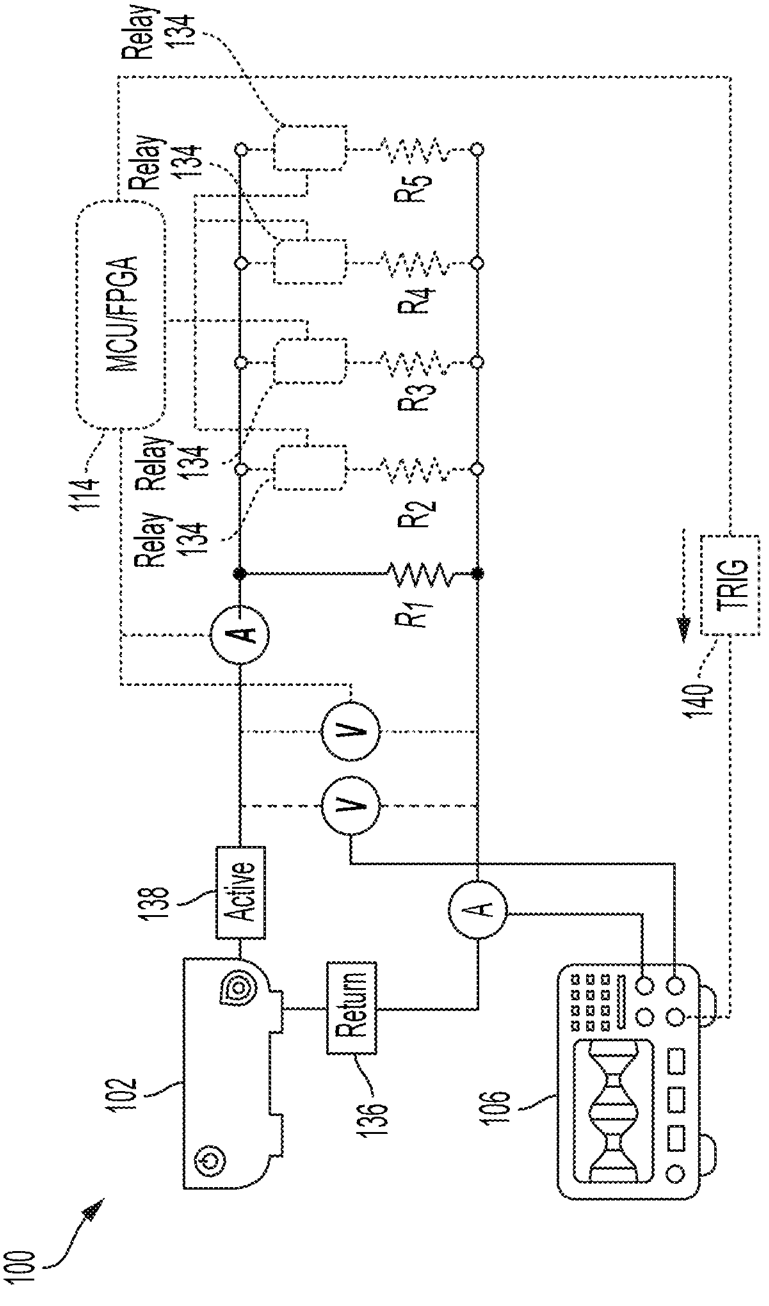
FIG. 4 is a schematic view of another embodiment of the testing system of FIG. 1.

FIG. 4 illustrates another embodiment of the testing system 100 including the generator 102, the simulated load 104, and the DAQ system 106. The DAQ system 106 in this illustrated embodiment is shown as an oscilloscope, but other DAQ systems can be used, such as analyzers or other type of electronic test equipment. The processor 120 of the simulated load 104 is shown in FIG. 2 as being either an MCU or an FPGA, but as discussed herein, various other configurations of the processor 120 are possible.

In this illustrated embodiment, the simulated load 104 includes a fixed resistance (including resistive component $R_1$) and a binary resistance (including resistive components $R_2$, $R_3$, $R_4$, and $R_5$) that are each similar to that discussed above with respect to FIG. 2. However, in this illustrated embodiment, the binary resistance includes four resistive components $R_2$ to $R_5$. The testing system 100 of FIG. 4 is thus a 4-bit testing system because the simulated load 104 includes four resistive components $R_2$ to $R_5$ that each have a binary state defined by whether its associated one of a plurality of relays 134 is on (relay switch closed and binary value 1) or off (relay switch open and binary value 0).

The fixed resistive component $R_1$ and the binary resistance's resistive components $R_2$ to $R_5$ can each have a variety of values. Table 3 shows one embodiment of resistance values (in Ohms) for the fixed resistive component $R_1$ and the binary resistance's resistive components $R_2$ to $R_5$. In an exemplary embodiment, as in Table 1, each of the binary resistance's resistive components $R_2$ to $R_5$ has a different resistance value, which allows each combination of relay 134 on/off states to have a different overall resistance value. If all of the plurality of relays 134 are in an off state, the simulated load 104 will still have a resistance defined by the fixed resistive component $R_1$ and thus avoid a short circuit condition.

TABLE 3

| | $R_1$ | $R_2$ | $R_3$ | $R_4$ | $R_5$ |
|---|---|---|---|---|---|
| Resistance | 500 | 200 | 150 | 100 | 30 |

The testing system 100 of FIG. 4 also illustrates locations of return and active electrodes 136, 138 of a bipolar electrosurgical instrument relative to the simulated load 104 and the generator 102. As will be appreciated by a person skilled in the art, energy (e.g., an electrical current) flows from the generator 102 and through the active electrode 138 to the load 104 and then flows through the return electrode 136 before returning to the generator 102 and, in testing, to the DAQ system 106. The return and active electrodes 136, 138 can be included in the testing system 100 as part of an electrosurgical instrument or can be independent elements used in the testing system 100 for testing purposes.

FIG. 4 also shows that the DAQ system 106 includes a trigger. The trigger is part of the oscilloscope 106 and functions according to a oscilloscope's trigger system, as will be appreciated by those skilled in the art, such as by being manually actuated (e.g., button pressed, switch flipped, etc.) by a user. As represented by a "TRIG" signal 140 shown in FIG. 4, actuation of the trigger is configured to trigger the DAQ system 106 to begin sampling the circuit signal and display information on the display 116 when the relays 134 have stabilized and are sensing power. The DAQ system 106 can be configured to use the trigger signal (also referred to as a "trigger pulse") to initiate a special memory capture. The special memory capture allows dividing the memory field of the DAQ system 106 into a series or sets of "frames" or "single captures" similar to how video is a collection of photographs collected at a fixed 24 hz/30 hz time interval. Typically electrosurgical energy delivery is about 10 seconds or less, and memory segmentation from external trigger(s) allows very high resolution data analysis of very complex signal responses. For example, 2,000 frames of eight periodic therapeutic waves can be captured about every 10-20 uSec and data can be captured about every 100-1500 us depending on tissue being simulated. The special memory capture of a DAQ system is referred to by different names by different vendors. For example, the special memory capture is referred to with respect to oscilloscopes available from different vendors as segmented memory (Keysight), FastFrame™ (Techtronix), sequence mode (Teledyne LeCroy), ultra-segmented mode (Rohde & Schwartz), and history memory mode (Yokogawa Test & Measurement Corporation).

A number of possible effective resistance options for a generator testing system is defined by a number of resistive components in the testing system's binary resistance. For example, the testing system 100 of FIG. 2 as a 12-bit testing system has 4,096 possible effective resistance and capacitance options. Using the embodiment of FIG. 2 with the resistance values of Table 1 as an example, all of the first plurality of relays 126 being on (enabled) offer an effective resistance of 4.5 Ohms despite the smallest singular resistive element being only 10 Ohms. With all twelve binary loads enabled by each of the first plurality of relays 126 being on, each of the twelve binary resistive components $R_0$ to Ru will share a load proportional to the individual impedance. With all of the first plurality of relays 126 being off (disabled), the fixed resistance of 2000 Ohms will be the dominating contributor and inhibit a short circuit condition. The fixed capacitive component $C_{fixed}$ and the twelve binary capacitive components $C_0$ to $C_{11}$ follow a similar example except that the fixed capacitive component $C_{fixed}$ is configured to tune out any undesired phase shift that may be caused by connection hardware and wiring. A "trimmer" or variable capacitor as the fixed capacitive component $C_{fixed}$ can be used to serve this purpose.

A generator testing system's algorithm (e.g., the algorithm 124 of FIG. 1, etc.) provides a selection algorithm that reduces the number of possible effective resistance options for a testing system from the number defined by the number of resistive components in the testing system's binary resistance to a much lower number based on "gray coding." For example, the 4,096 possible effective resistance and capacitance options of a 12-bit testing system such as the testing system 100 of FIG. 2 can be reduced to 20 to 100 options in a predefined lookup table based on "gray coding." Gray coding is a method toggling logical operations or "bits" by minimization of number bit transitioning from a 0 to 1 to either a singular bit (or a pair or, in some instances, a trio.) Classical binary coding allows for full toggling of all 12 bits in this example of FIG. 2, which can shorten life of relays and cause extreme ripple or chattering of output.

Figure 5:
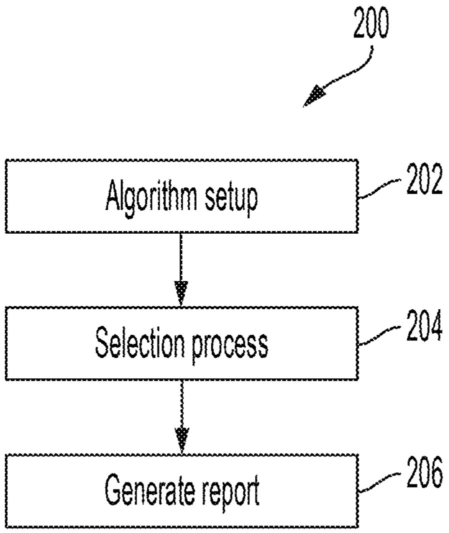
FIG. 5 is a flowchart showing one embodiment of a method of testing an electrosurgical generator.

FIG. 5 illustrates one embodiment of a method 200 of setting up and using an algorithm for testing an electrosurgical generator. The method 200 is described with respect to the testing system 100 of FIGS. 1 and 2 for ease of explanation but can be used similarly with other electrosurgical generator testing systems. In general, the method 200 includes setup 202, selection 204, and generation 206.

Figure 6:
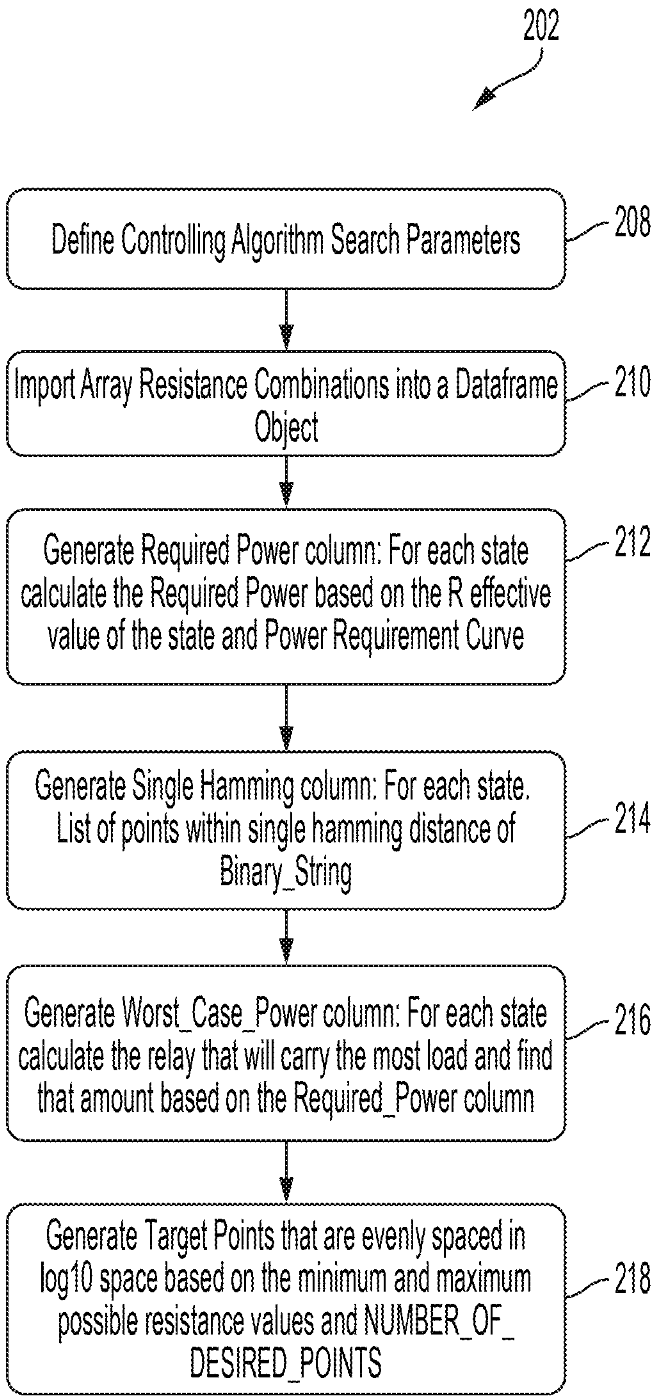
FIG. 6 is a flowchart showing one embodiment of a method of algorithm setup in the method of FIG. 5.

The method 200 includes setting up 202 the algorithm 124. The algorithm 124 is set up 202 prior to the generator 102 providing energy to the simulated load 104 for testing purposes. FIG. 6 illustrates one embodiment of setting up 202 the algorithm 124.

As shown in FIG. 6, setting up 202 the algorithm 124 includes defining 208 controlling algorithm search parameters. The defining 208 requires user input of the parameters to the simulated load 104, e.g., using an I/O unit of the computer system to store the parameters in the memory 118. In an exemplary embodiment, at least some of the parameters input by a user are a load profile based on generator parameters gathered during energy delivery to an actual tissue load (e.g., stomach tissue, uterine tissue, vessels, etc.). In an exemplary embodiment, the parameters include a size of the binary resistance array in bits (e.g., 4-bit, 5-bit, 6-bit, etc.), a number of desired points in a planned trajectory, a file path to a file of binary combinations, a hamming limit defining an allowable hamming distance for automatic selection in the selection 204, an allowable resistance percentage defining limits for automatic selection in the selection 204 and a basis for filter for manual selection in the selection 204, a power limit defining a maximum allowable power to a single resistor stack, and a power requirement curve. The power requirement curve can be calculated by the following:

$$\text{Required Power} = \{\text{Initial Power } R < \text{Cutoff Initial Power} * \exp(-\text{Rate of Decay} * (R - \text{Cutoff}))R \geq \text{Cutoff}\}$$

Once the parameters including at least the file path have been input, the array resistance combinations is imported 210 into a dataframe object, e.g., for storage in the memory 118. Table 4 below shows one example of a file that may be imported 210 for an 8-bit testing system, with resistance being in Ohms.

TABLE 4

| DEC | Binary | $R_7$ | $R_6$ | $R_5$ | $R_4$ | $R_3$ | $R_2$ | $R_1$ | $R_0$ | $R_{fixed}$ | $R_{effective}$ |
|---|---|---|---|---|---|---|---|---|---|---|---|
| 0 | 00000000 | 0 | 0 | 0 | 0 | 0 | 0 | 0 | 0 | 2000 | 2000 |
| 1 | 00000001 | 0 | 0 | 0 | 0 | 0 | 0 | 0 | 10 | 2000 | 10 |
| 2 | 00000010 | 0 | 0 | 0 | 0 | 0 | 0 | 20 | 0 | 2000 | 19.8 |
| 3 | 00000011 | 0 | 0 | 0 | 0 | 0 | 0 | 20 | 10 | 2000 | 6.6 |
| 4 | 00000100 | 0 | 0 | 0 | 0 | 0 | 33.33333 | 0 | 0 | 2000 | 32.8 |
| 5 | 00000101 | 0 | 0 | 0 | 0 | 0 | 33.33333 | 0 | 10 | 2000 | 7.7 |
| 6 | 00000110 | 0 | 0 | 0 | 0 | 0 | 33.33333 | 20 | 0 | 2000 | 12.4 |

Setting up 202 the algorithm 124 also includes generating 212 (e.g., by the processor 120) required power for each of the binary states based on the effective resistance value ($R_{effective}$) for the binary state and on the power requirement curve. Seven binary states (0-6) are in the example of Table 4.

Setting up 202 the algorithm 124 also includes generating 214 (e.g., by the processor 120) single hamming values for each of the binary states. The single hamming values includes a list of binary states (0 or 1) within a single hamming distance of a particular binary string. For example, for a binary state of 11111111, the single hamming values generated would be 01111111, 10111111, 11011111, 11101111, 11110111, 11111011, 11111101, and 11111110.

Setting up 202 the algorithm 124 also includes generating 216 (e.g., by the processor 120) a worst case power value for each of the binary states. Generating 216 the worst case power value for a binary state includes calculating which of the plurality of relays associated with the plurality of binary resistive components will carry the most load.

Figure 7:
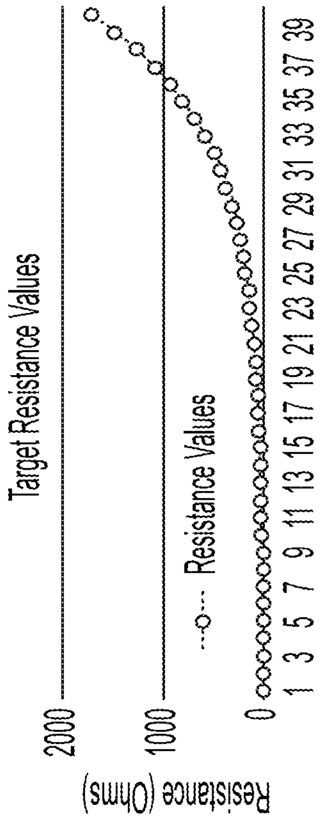
FIG. 7 is a graph showing one embodiment of target resistance values versus resistance.
Figure 8:
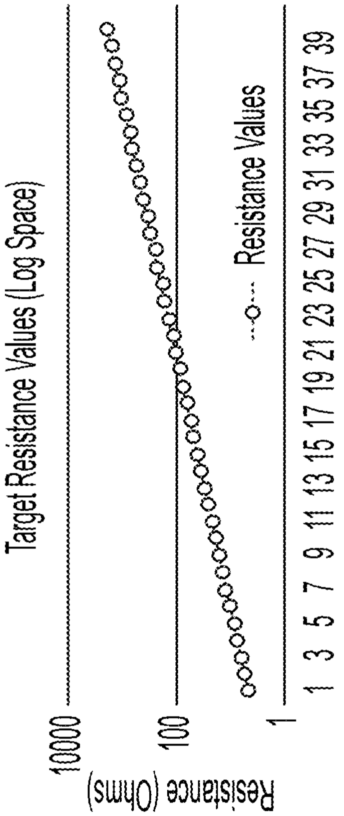
FIG. 8 is a graph showing one embodiment of target resistance values versus resistance in log space.
Figure 9:
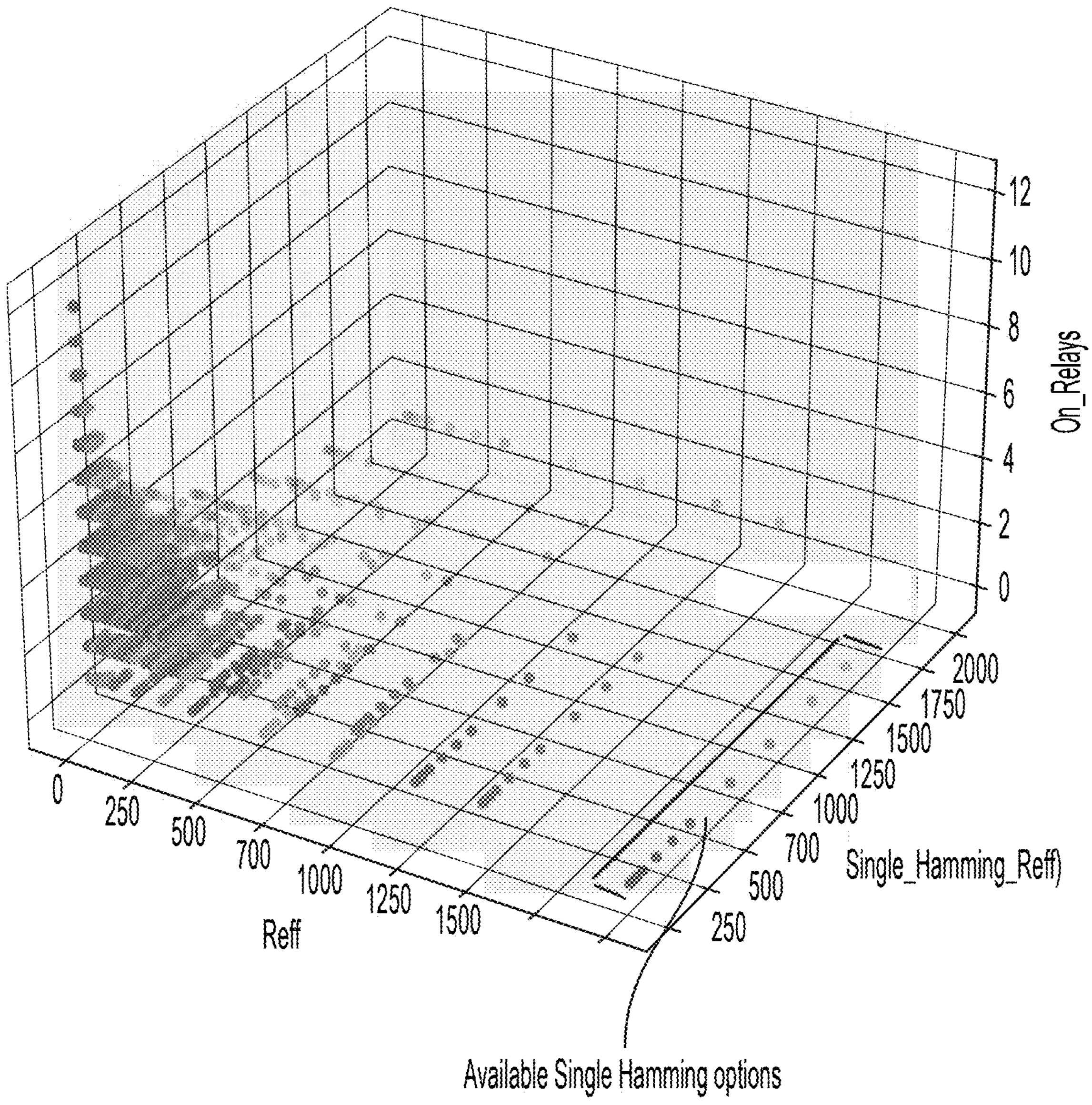
FIG. 9 is a three-dimensional graph showing one embodiment of effective resistance versus number of on (enabled) relays versus available single hamming options.

Setting up 202 the algorithm 124 also includes generating 218 (e.g., by the processor 120) target points that are evenly spaced based on the minimum and maximum possible effective resistance values (e.g., 6.6 Ohms and 2000 Ohms in the example of Table 4) and the number of desired points previously defined 208. FIGS. 7-9 illustrate one embodiment of generated 218 target points. FIGS. 7-9 show that the gray coding provides for a denser availability of options at lower resistance values than at higher resistance values. At low resistance, many relays being on for the binary resistance is ideal for load sharing. Also at low resistance, density of options is ideal for the exponential resistance target curve (see FIG. 8).

Figure 10:
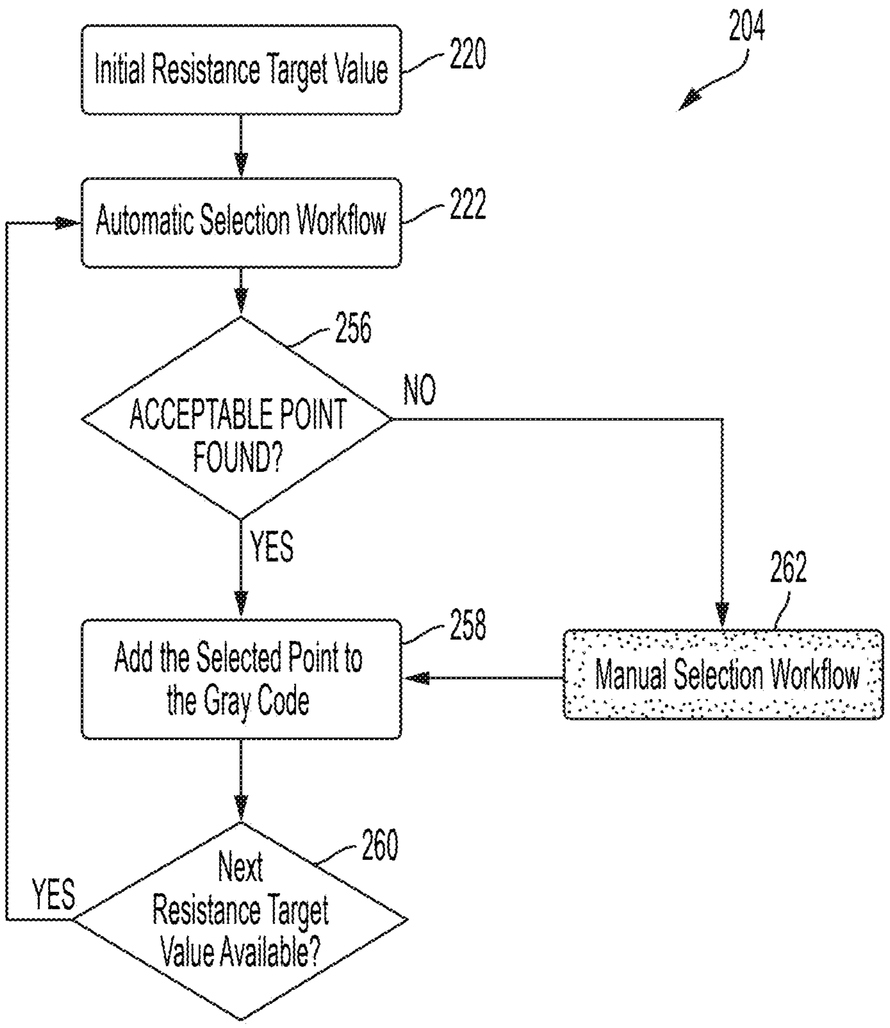
FIG. 10 is a flowchart showing one embodiment of a method of a selection process in the method of FIG. 5.

Referring again to FIG. 5, after the algorithm 124 has been set up 202, a selection process if performed 204. Performing 204 the selection process includes executing the algorithm, which was previously set up 202, to test an electrosurgical generator (e.g., executing the algorithm 124 of FIG. 1 to test the electrosurgical generator 102). FIG. 10 illustrates one embodiment of performing 204 the selection process.

Figure 11A:
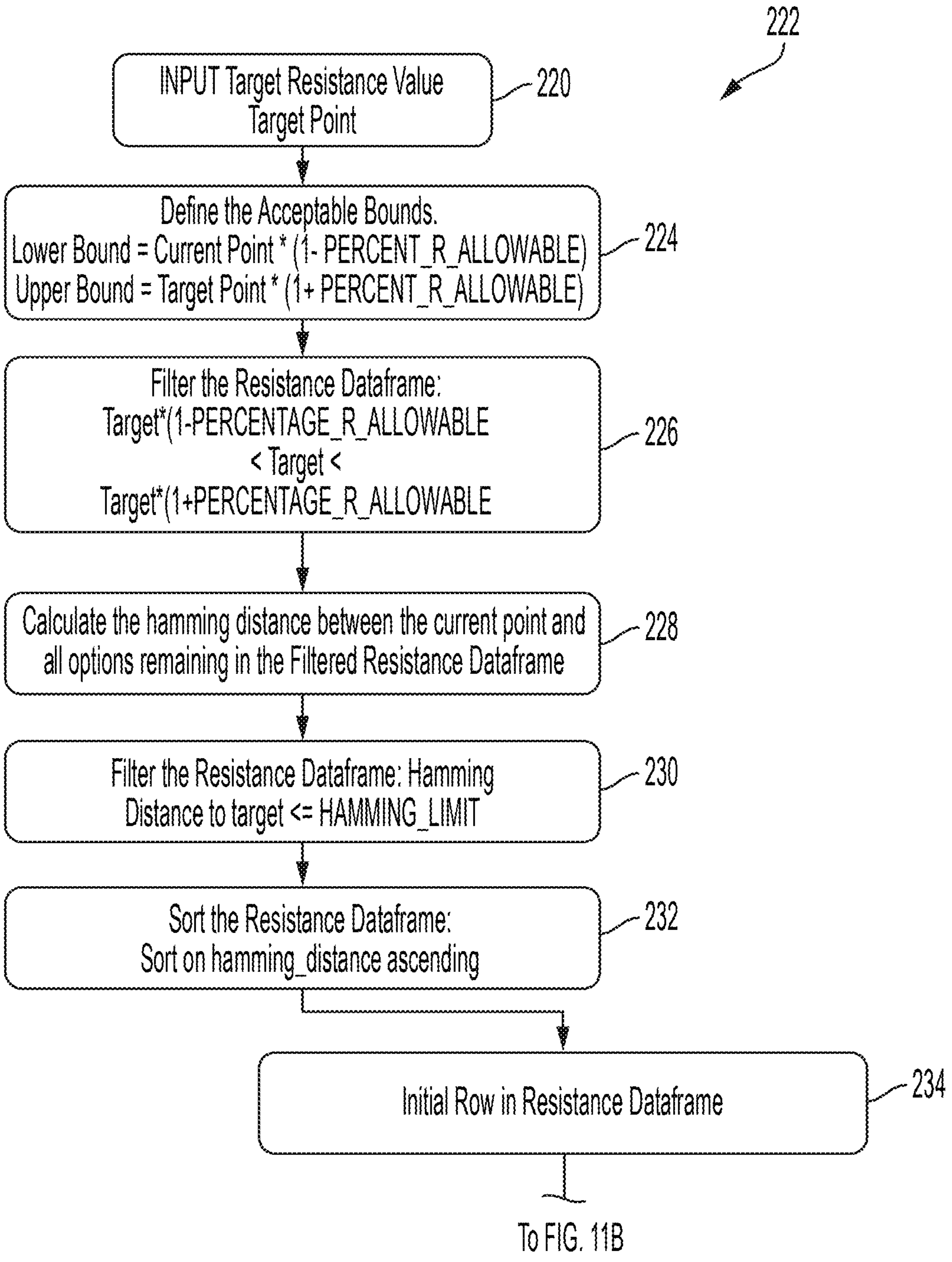
FIG. 11A is a first portion of a flowchart showing one embodiment of a method of an automatic selection workflow in the method of FIG. 10.
Figure 11B:
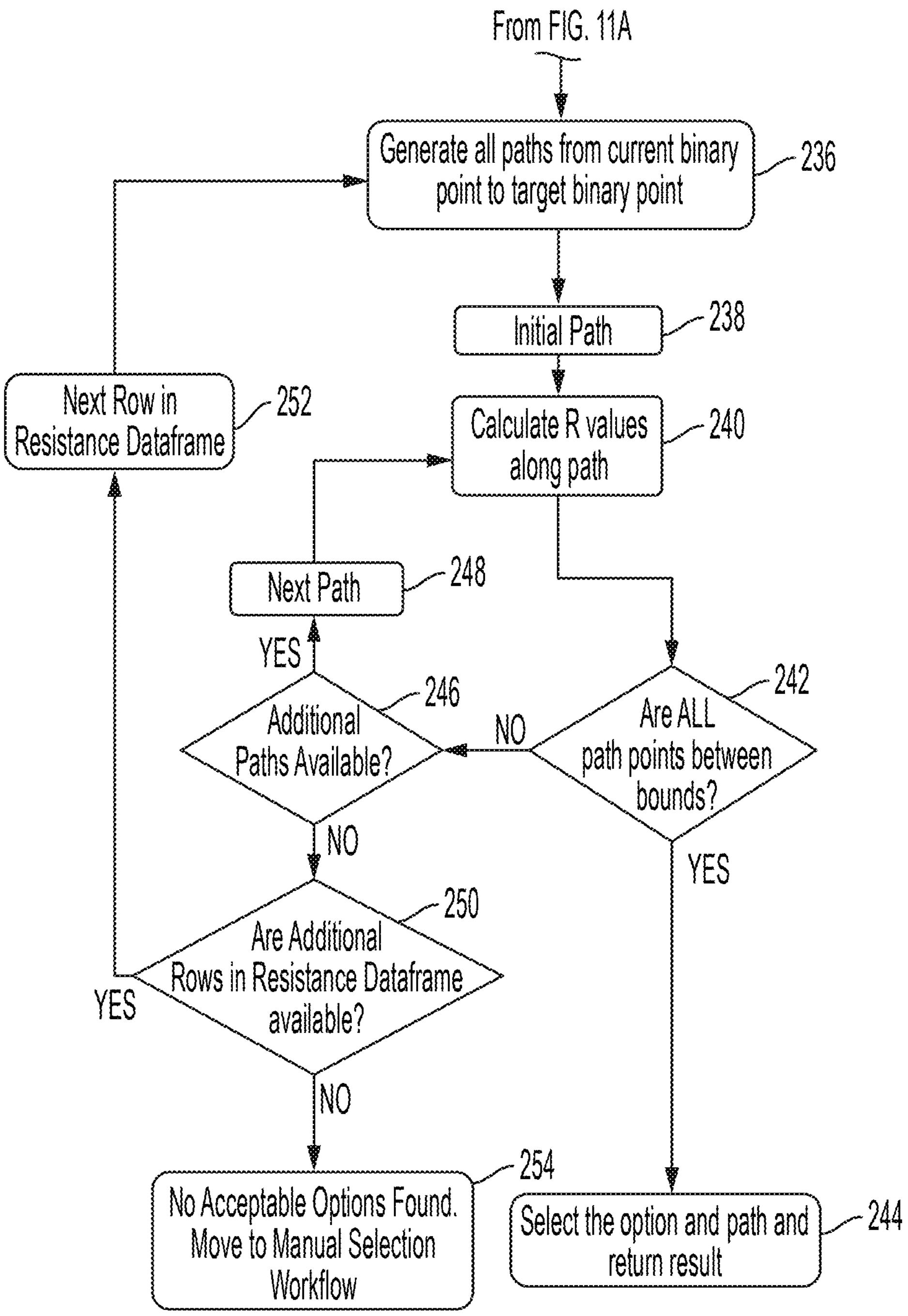
FIG. 11B is a second portion of the flowchart of FIG. 11A.

Performing 204 the selection process includes inputting 220 an initial one of the generated 218 target points. An automatic selection workflow is then performed 222 to tune the load to the input 220 one of the target points and identify an acceptable point. The selection workflow is considered "automatic" because it is executed by a processor (e.g., the processor 120 of the simulated load 104) and selects an acceptable point without user input. FIGS. 11A and 11B illustrate one embodiment of performing 222 the automatic selection.

As shown in FIGS. 11A and 11B, the automatic selection workflow includes defining 224 acceptable bounds with a lower acceptable bound being based on the current point and an upper acceptable bound being based on the initial one of the generated 218 target points (also referred to herein as the "initial target point"). The current point is the current binary state (e.g., state of the 4 bits defined by the binary resistance in the 4-bit system, state of the 12 bits defined by the binary resistance in a 12-bit system, etc.) The lower acceptable bound equals the current point multiplied by (1 minus the allowable resistance percentage defining limits for automatic selection that was input when setting up 202 the algorithm). The upper acceptable bound equals the initial target point multiplied by (1 plus the allowable resistance percentage defining limits for automatic selection that was input when setting up 202 the algorithm).

The automatic selection workflow also includes filtering 226 the resistance dataframe according to the following formula, where "Target" is the initial target point: Target*(1 minus the allowable resistance percentage defining limits for automatic selection that was input when setting up 202 the algorithm)<Target<Target*(1 plus the allowable resistance percentage defining limits for automatic selection that was input when setting up 202 the algorithm).

The automatic selection workflow also includes calculating 228 the hamming distance between the current point and all options remaining in the filtered 226 resistance dataframe. For example, for a current point of 01110111 and an initial target point of 11110011 the hamming distance is calculated to be two because only two binary values in the binary string, the first and sixth binary values, need to be changed to move from the current point to the initial target point, e.g., 01110111 to 11110111 to 11110011, or 01110111 to 01110011 to 11110011.

The resistance dataframe is then filtered 230 again according to the following formula, where "Target" is the initial target point: calculated 228 hamming distance to target <=the hamming limit that was input when setting up 202 the algorithm. The filtered 230 resistance dataframe is then sorted 232 in ascending order. The initial row in the resistance dataframe in the sorted 232 list is considered 234 the current binary point (also referred to herein as "current point").

The automatic selection workflow also includes generating 236 all possible paths from the current binary point to the target binary point, which is initially the initial target point. Table 5 shows one example of generating 236 all paths from the current binary point (01110111) to the target binary point (11110011) in an 8-bit system.

TABLE 5

| | Path 1 | Path 2 |
|---|---|---|
| Current Point | 01110111 | 01110111 |
| | 11110111 | 01110011 |
| Target Point | 11110011 | 11110011 |

Each of the generated paths is considered 238 in a preset order, which in this illustrated embodiment is the order of their generation. Consideration 238 thus begins with Path 1 (initial path generated 236). Resistance values are calculated 240 for each point along Path 1. If all of the calculated 240 resistance values are determined 242 to be within the previously defined lower and upper bounds, then Path 1 is an acceptable path and is selected 244 as the acceptable option and the selection process 204 continues (see FIG. 10) as discussed further below.

If all of the calculated 240 resistance values are not determined 242 to be within the previously defined lower and upper bounds, e.g., at least one of the resistance values is out of bounds, then Path 1 is not an acceptable path. If additional paths are available (e.g., at least two possible paths were generated 236 and at least one of the possible paths has not yet been considered 238), then the next path (e.g., Path 2 in this example) is considered 248, with resistance values being calculated 240 for each point along the path. If additional paths are not available (e.g., only one path was generated 236 or all of multiple generated 236 possible paths have been considered 238/248), then the automatic selection workflow includes determining 250 whether there are any additional rows available in the resistance dataframe. If there is at least one additional row available in the resistance dataframe, then the next row in the resistance dataframe is set 252 as the current binary point and the automatic selection workflow continues with all paths being generated 236 for the current binary point. Each of the rows in the resistance dataframe can thus be sequentially considered. If there is not at least one additional row available in the resistance dataframe, then no acceptable options have been identified 254 in the automatic selection workflow and the selection process 204 continues.

Referring again to FIG. 10, the selection process 204 includes determining 256 whether an acceptable path has been found in the performance 222 of the automatic selection workflow. If an acceptable path has been found (e.g., selected 244 in the automatic selection workflow), then the selected 244 path is added 258 to the gray code. Then, if it determined 260 that a next resistance target value is available, e.g., more than one target point was generated 218 and at least one generated 218 target point has not yet gone through the selection process), then the selection process 204 continues by subjecting the next resistance target value to the automatic selection workflow as discussed above. If it determined 260 that a next resistance target value is not available, e.g., all generated 218 target points have gone through the selection process, then the selection process 204 has completed and the method 200 continues with the generation 206, as discussed further below.

Figure 12A:
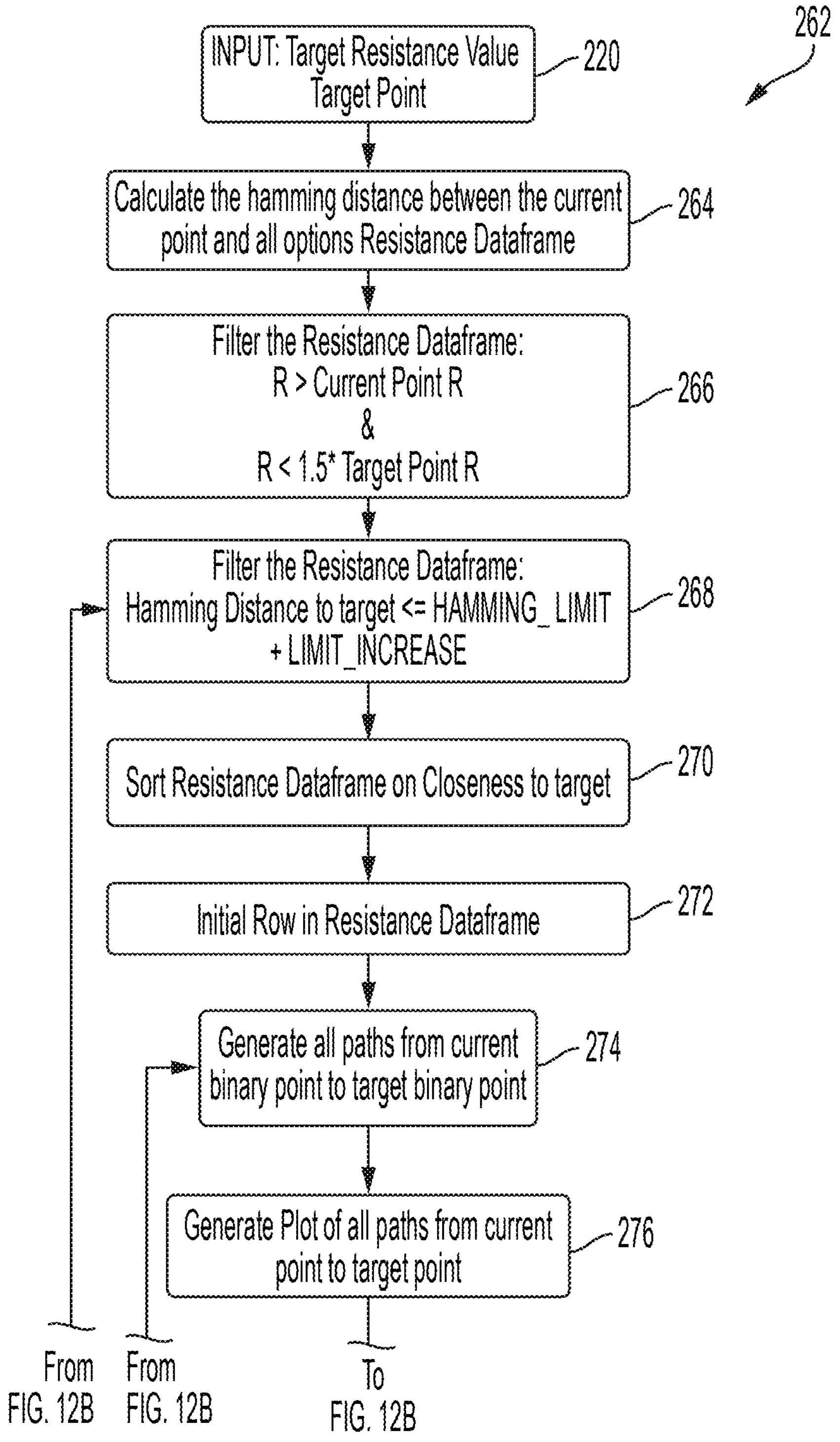
FIG. 12A is a first portion of a flowchart showing one embodiment of a method of a manual selection workflow in the method of FIG. 10.
Figure 12B:
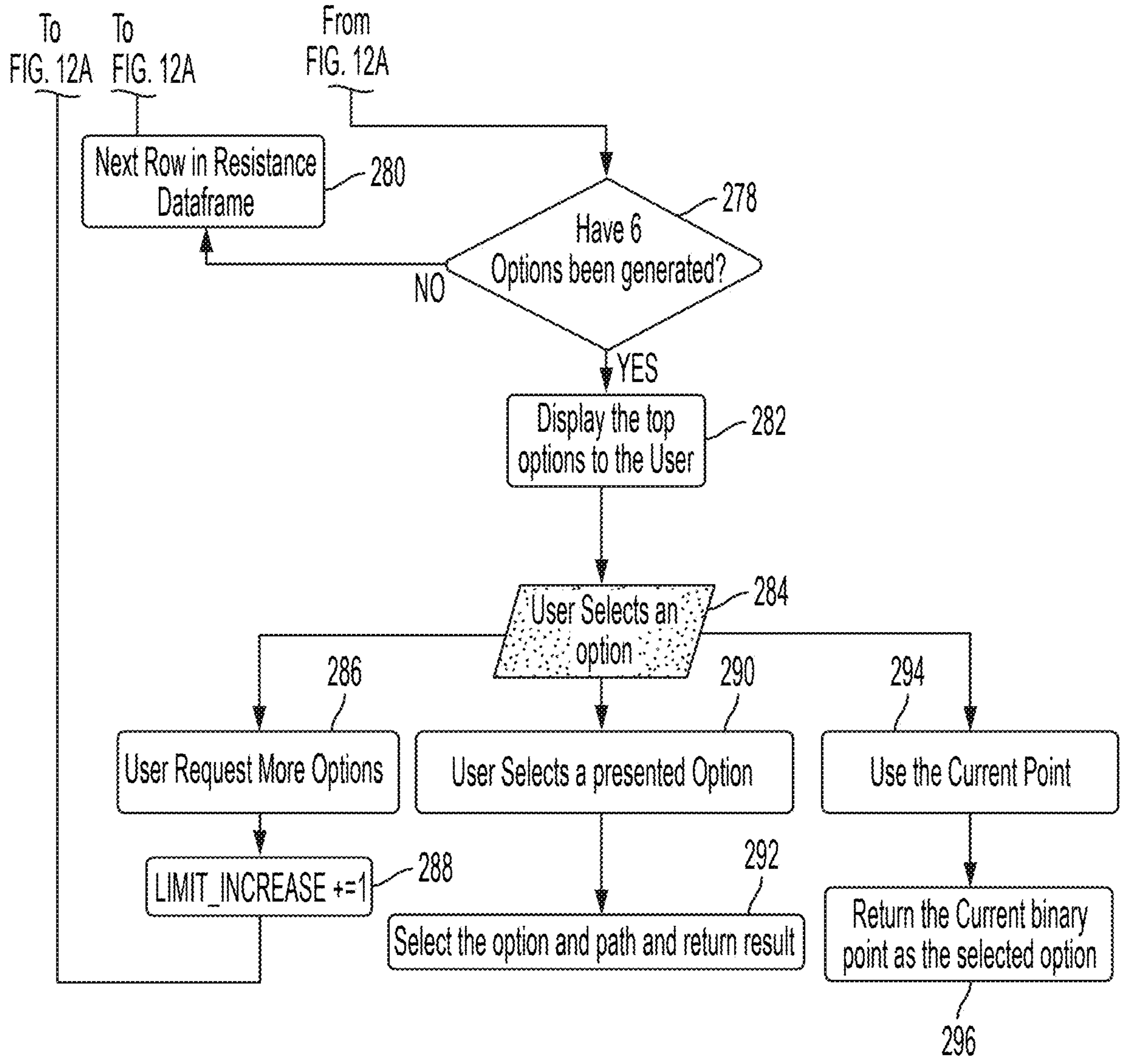
FIG. 12B is a second portion of the flowchart of FIG. 12A.

If an acceptable path has not been found (e.g., no selection 244 made in the automatic selection workflow), then a manual selection workflow is performed 262. The manual selection workflow requires a user to manually select an acceptable path. FIGS. 12A and 12B illustrate one embodiment of performing 262 the manual selection.

As shown in FIGS. 12A and 12B, the manual selection workflow includes calculating 264 the hamming distance between the current point and all options in the resistance dataframe, similar to the calculating 228 of FIGS. 11A and 11B discussed above.

The manual selection workflow also includes filtering 266 the resistance dataframe according to the following formula: R>Current Point R & R<1.5*Target Point. The resistance dataframe is then filtered 268 again according to the following formula: calculated 264 hamming distance to target <=the hamming limit that was input when setting up 202 the algorithm plus a preset limit increase value. The filtered 268 resistance dataframe is then sorted 270 on closeness to target. The initial row in the resistance dataframe in the sorted 270 list is considered 272 the current binary point.

The manual selection workflow also includes generating 274 all possible paths from the current binary point to the target binary point, which is initially the initial target point, similar to the generating 236 of FIGS. 11A and 11B discussed above. A plot is then generated 276 of all paths from the current binary point to the target binary point.

The manual selection workflow also includes determining 278 whether a predetermined plural number of options have been generated 274. The predetermined plural number in this illustrated embodiment is six, which should provide the user with varying enough options to select 284 from. If the predetermined plural number of options have not been generated 274, then a next row in the resistance dataframe in the sorted 270 list is considered 280 as the current binary point and the manual selection workflow continues by generating 274 all possible paths from the current binary point to the target binary point as discussed above.

If the predetermined plural number of options have been generated 274, then the plots for the predetermined plural number of options that have been generated 274 are shown to the user, e.g., on a display of the simulated load 104. The user then selects 284 one of the predetermined plural number of options as the acceptable path. As in this illustrated embodiment, the user can be presented with a variety of choices in making a selection 284. The user can either choose to request 286 more options, to select 290 one of the presented options, or to use 294 the current point instead of any of the presented options. If the user requests 286 more options, then the preset limit increase value is increased 288 by one and the manual selection workflow continues with filtering 268 the reference dataframe according to the following formula: calculated 264 hamming distance to target<=the hamming limit that was input when setting up 202 the algorithm plus a preset limit increase value. If the user selects 290 one of the presented options, then the selected 290 option is set 292 as the acceptable option and the selection process 204 continues by adding 258 the selected 290 path to the gray code as discussed above. If the user chooses to use 294 the current point instead of any of the presented options, then the current point is set 296 as the acceptable option and the selection process 204 continues by adding 258 the selected path to the gray code as discussed above.

Figure 13:
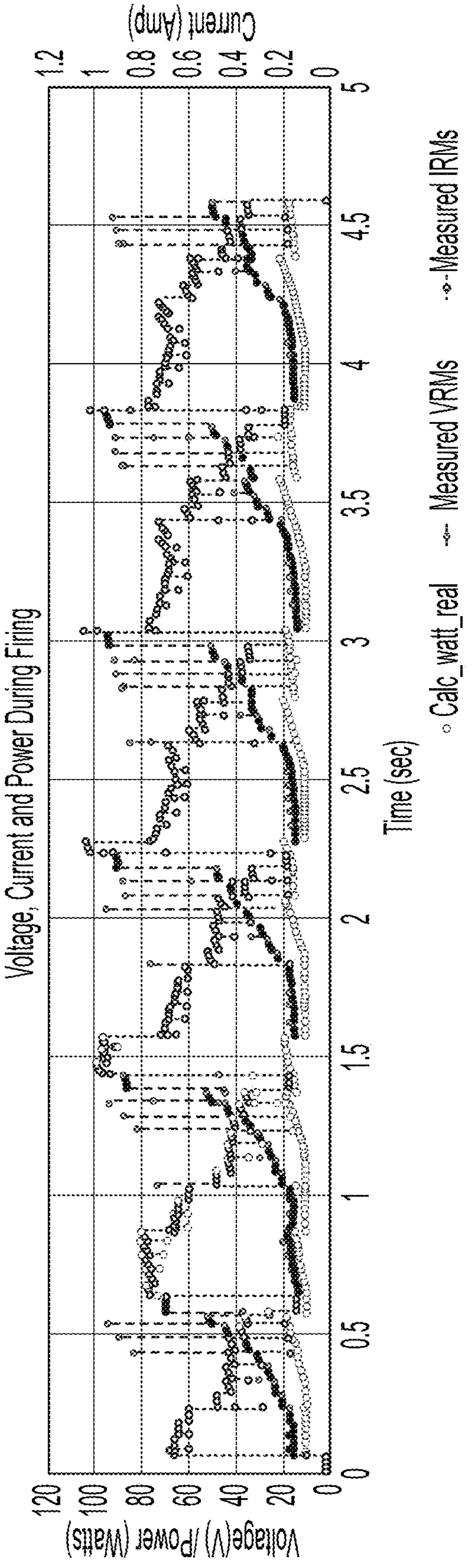
FIG. 13 is one embodiment of a graph showing voltage, current, and power during firing in which voltage, current, and power are plotted versus time.
Figure 14:
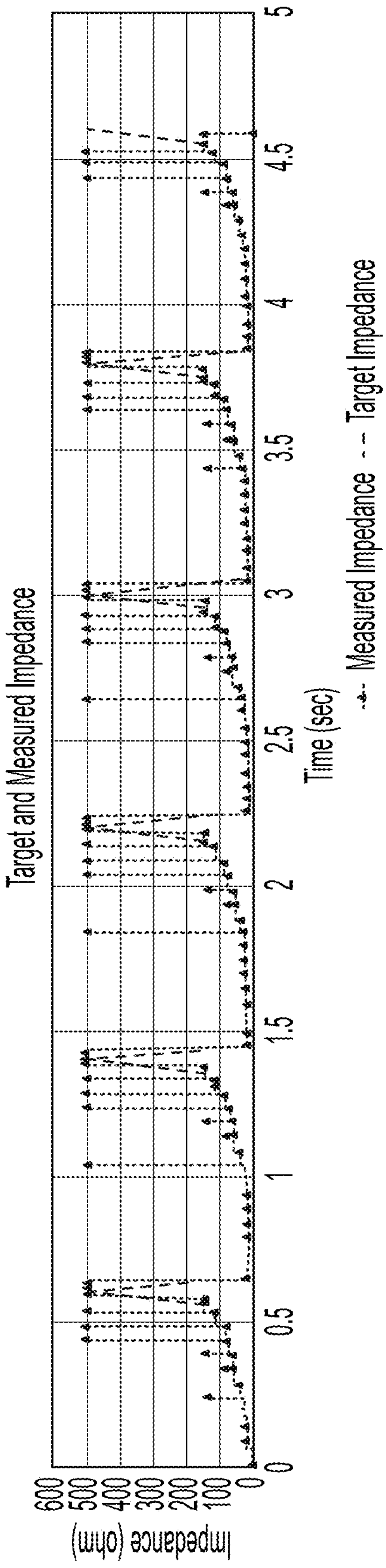
FIG. 14 is one embodiment of a graph showing target and measured impedance in which target and measured impedance are plotted versus time.

Referring again to FIG. 5, after the selection process has been performed 204, a report is generated 206 indicating results of the generator testing. In an exemplary embodiment, the report correlates the identified acceptable points for each of the generated 218 target points to the generator settings (e.g., voltage, current, and derived impedance and phase signals) that allow that identified acceptable point to be achieved. The report can be provided as a graph and/or as a table. FIGS. 13 and 14 illustrate embodiments of graphs that can be provided in the report. FIG. 13 illustrates one embodiment of a graph showing voltage, current, and power during firing in which voltage, current, and power are plotted versus time. FIG. 14 illustrates one embodiment of a graph showing target and measured impedance in which target and measured impedance are plotted versus time.

As mentioned above, a computer system may be suitable for use in implementing computerized components described herein. In broad overview of an exemplary embodiment, the computer system includes a processor configured to perform actions in accordance with instructions, and memory devices configured to store instructions and data. The processor is in communication, via a bus, with the memory (and/or incorporates the memory) and with at least one network interface controller with a network interface for connecting to external devices, e.g., a computer system (such as a mobile phone, a tablet, a laptop, a server, etc.). The processor is also configured to be in communication, via the bus, with any other processor(s) of the computer system and with any I/O devices at an I/O interfaces. Generally, a processor will execute instructions received from the memory. In some embodiments, the computer system can be configured within a cloud computing environment, a virtual or containerized computing environment, and/or a web-based microservices environment.

In more detail, the processor can be any logic circuitry that processes instructions, e.g., instructions fetched from the memory. In many embodiments, the processor is an embedded processor, a microprocessor unit (MPU), microcontroller unit (MCU), field-programmable gate array (FPGA or FGPA), or special purpose processor. The computer system can be based on any processor, e.g., suitable digital signal processor (DSP), or set of processors, capable of operating as described herein. In some embodiments, the processor can be a single core or multi-core processor. In some embodiments, the processor can be composed of multiple processors.

The memory can be any device suitable for storing computer readable data. The memory can be a device with fixed storage or a device for reading removable storage media. Examples include all forms of non-volatile memory, media and memory devices, semiconductor memory devices (e.g., EPROM, EEPROM, SDRAM, flash memory devices, and all types of solid state memory), magnetic disks, and magneto optical disks. A computer system can have any number of memory devices.

The memory also can include a cache memory, which is generally a form of high-speed computer memory placed in close proximity to the processor for fast read/write times. In some implementations, the cache memory is part of, or on the same chip as, the processor.

The network interface controller is configured to manage data exchanges via the network interface. The network interface controller handles the physical, media access control, and data link layers of the Open Systems Interconnect (OSI) model for network communication. In some implementations, some of the network interface controller's tasks are handled by the processor. In some implementations, the network interface controller is part of the processor. In some implementations, a computer system has multiple network interface controllers. In some implementations, the network interface is a connection point for a physical network link, e.g., an RJ 45 connector. In some implementations, the network interface controller supports wireless network connections and an interface port is a wireless Bluetooth transceiver. Generally, a computer system can be configured to exchange data with other network devices via physical or wireless links to a network interface. In some implementations, the network interface controller implements a network protocol such as LTE, TCP/IP Ethernet, IEEE 802.11, IEEE 802.16, Bluetooth, or the like.

In some uses, the I/O interface supports an input device and/or an output device (not shown). In some uses, the input device and the output device are integrated into the same hardware, e.g., as in a touch screen. In some uses, such as in a server context, there is no I/O interface or the I/O interface is not used. In some uses, additional other components are in communication with the computer system, e.g., external devices connected via a universal serial bus (USB). In some implementations an I/O device is incorporated into the computer system, e.g., a touch screen on a tablet device.

In some implementations, a computer device 210 includes an additional device such as a co-processor, e.g., a math co-processor that is configured to assist the processor with high precision or complex calculations.

One skilled in the art will appreciate further features and advantages of the devices, systems, and methods based on the above-described embodiments. Accordingly, this disclosure is not to be limited by what has been particularly shown and described, except as indicated by the appended claims. All publications and references cited herein are expressly incorporated herein by reference in their entirety for all purposes.

The present disclosure has been described above by way of example only within the context of the overall disclosure provided herein. It will be appreciated that modifications within the spirit and scope of the claims may be made without departing from the overall scope of the present disclosure.

What is claimed is:

1. An electrosurgical generator testing system, comprising:

a simulated tissue load configured to be operatively coupled to an electrosurgical generator configured to deliver energy to an electrosurgical instrument, the simulated tissue load comprising:

a circuit including a first plurality of relays and a plurality of resistive components, the plurality of resistive components being arranged in parallel, and each of the plurality of relays being operatively coupled to an associated one of the plurality of resistive components such that each of the plurality of resistive components is either enabled or disabled based on a state of its associated one of the first plurality of relays, a processor, and a memory storing instructions that, when executed by the processor, cause the processor to perform operations comprising:

with the simulated tissue load receiving an energy signal from the electrosurgical generator, controlling the state of each of the first plurality of relays so as to sequentially simulate a plurality of target tissue loads, each target tissue load of the plurality of target tissue loads being defined by a plurality of predefined parameters stored in the memory, and generating a report indicative of settings of the electrosurgical generator for each of the simulated plurality of target tissue loads.

2. The electrosurgical generator testing system of claim 1, wherein the simulated tissue load further comprises an additional resistive component having a fixed resistance, the additional resistive component being arranged in parallel with the plurality of resistive components.

3. The electrosurgical generator testing system of claim 1, wherein the simulated tissue load further comprises a second plurality of relays and a plurality of capacitive components, the plurality of capacitive components being arranged in parallel with each other and with the plurality of resistive components.

4. The electrosurgical generator testing system of claim 3, wherein the simulated tissue load further comprises an additional capacitive component having a fixed capacitance, the additional capacitive component being arranged in parallel with the plurality of capacitive components.

5. The electrosurgical generator testing system of claim 1, wherein the plurality of resistive components includes a number of resistive components in a range of four to thirty-two; and each of the plurality of resistive components includes a resistor.

6. The electrosurgical generator testing system of claim 1, wherein the setting of the electrosurgical generator for each of the simulated plurality of target tissue loads is either:

automatically selected through the controlling of the state of each of the first plurality of relays, or manually selected by a user.

7. The electrosurgical generator testing system of claim 6, wherein the operations further comprise:

prompting the user to manually select the setting of the electrosurgical generator for one of the simulated plurality of target tissue loads in response to the setting of the electrosurgical generator for the one of the simulated plurality of target tissue loads being unable to be automatically selected through the controlling of the state of each of the first plurality of relays.

8. The electrosurgical generator testing system of claim 1, further comprising the electrosurgical generator.

9. The electrosurgical generator testing system of claim 1, further comprising a data acquisition system (DAQ) configured to be operatively coupled to the simulated tissue load and to display information indicative of data in the generated report.

10. The electrosurgical generator testing system of claim 9, further comprising the electrosurgical generator.

11. A method of testing electrosurgical generators, comprising:

receiving an electrical signal from an electrosurgical generator at a circuit of a simulated tissue load, the circuit including a first plurality of relays and a plurality of resistive components, the plurality of resistive components being arranged in parallel, and each of the plurality of relays being operatively coupled to an associated one of the plurality of resistive components such that each of the plurality of resistive components is either enabled or disabled based on a state of its associated one of the first plurality of relays;

with the simulated tissue load receiving the energy signal from the electrosurgical generator, controlling, using a processor, the state of each of the first plurality of relays so as to sequentially simulate a plurality of target tissue loads, each target tissue load of the plurality of target tissue loads being defined by a plurality of predefined parameters stored in a memory of the simulated tissue load, and generating, using the processor, a report indicative of settings of the electrosurgical generator for each of the simulated plurality of target tissue loads.

12. The method of claim 11, wherein the simulated tissue load further comprises an additional resistive component having a fixed resistance, the additional resistive component being arranged in parallel with the plurality of resistive components.

13. The method of claim 11, wherein the simulated tissue load further comprises a second plurality of relays and a plurality of capacitive components, the plurality of capacitive components being arranged in parallel with each other and with the plurality of resistive components.

14. The method of claim 13, wherein the simulated tissue load further comprises an additional capacitive component having a fixed capacitance, the additional capacitive component being arranged in parallel with the plurality of capacitive components.

15. The method of claim 11, wherein the plurality of resistive components includes a number of resistive components in a range of four to thirty-two; and each of the plurality of resistive components includes a resistor.

16. The method of claim 11, wherein the setting of the electrosurgical generator for each of the simulated plurality of target tissue loads is either:

automatically selected through the controlling of the state of each of the first plurality of relays, or manually selected by a user.

17. The method of claim 16, further comprising prompting, using the processor, the user to manually select the setting of the electrosurgical generator for one of the simulated plurality of target tissue loads in response to the setting of the electrosurgical generator for the one of the simulated plurality of target tissue loads being unable to be automatically selected through the controlling of the state of each of the first plurality of relays.

18. The method of claim 11, further comprising displaying, on a data acquisition system (DAQ) operatively coupled to the simulated tissue load, information indicative of data in the generated report.

19. A non-transitory computer program product storing instructions which, when executed by a processor, cause the processor to implement operations comprising:

with a simulated tissue load receiving an energy signal from the electrosurgical generator, controlling a state of each of a first plurality of relays of the simulated tissue load so as to sequentially simulate a plurality of target tissue loads, each target tissue load of the plurality of target tissue loads being defined by a plurality of predefined parameters stored in a memory of the simulated tissue load, the circuit including the first plurality of relays and a plurality of resistive components, the plurality of resistive components being arranged in parallel, and each of the plurality of relays being operatively coupled to an associated one of the plurality of resistive components such that each of the plurality of resistive components is either enabled or disabled based on the state of its associated one of the first plurality of relays; and generating a report indicative of settings of the electrosurgical generator for each of the simulated plurality of target tissue loads.

* * * * *